(12) United States Patent
Kasargod et al.

(10) Patent No.: US 9,843,501 B2
(45) Date of Patent: Dec. 12, 2017

(54) SYSTEMS AND METHODS FOR INCORPORATING DEVICES INTO A MEDICAL DATA NETWORK

(71) Applicant: QUALCOMM Incorporated, San Diego, CA (US)

(72) Inventors: Kabir Suresh Kasargod, San Diego, CA (US); Eugene Dantsker, San Diego, CA (US); Muhammed Ibrahim Sezan, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 293 days.

(21) Appl. No.: 14/790,093

(22) Filed: Jul. 2, 2015

(65) Prior Publication Data
US 2017/0005911 A1 Jan. 5, 2017

(51) Int. Cl.
| | |
|---|---|
| G06F 15/173 | (2006.01) |
| H04L 12/721 | (2013.01) |
| G06F 19/00 | (2011.01) |
| H04W 12/02 | (2009.01) |
| H04W 40/02 | (2009.01) |
| H04L 12/725 | (2013.01) |
| A61B 5/00 | (2006.01) |
| H04L 12/715 | (2013.01) |
| H04L 12/717 | (2013.01) |
| H04L 29/08 | (2006.01) |
| H04L 29/06 | (2006.01) |
| H04W 84/18 | (2009.01) |

(52) U.S. Cl.
CPC ............ *H04L 45/14* (2013.01); *A61B 5/0006* (2013.01); *G06F 19/3418* (2013.01); *H04L 45/306* (2013.01); *H04L 45/42* (2013.01); *H04L 45/64* (2013.01); *H04L 67/12* (2013.01); *H04L 69/24* (2013.01); *H04W 12/02* (2013.01); *H04W 40/02* (2013.01); *A61B 5/0008* (2013.01); *H04L 45/127* (2013.01); *H04L 63/205* (2013.01); *H04L 67/322* (2013.01); *H04W 84/18* (2013.01)

(58) Field of Classification Search
None
See application file for complete search history.

(56) References Cited

U.S. PATENT DOCUMENTS

| | | | |
|---|---|---|---|
| 8,798,760 B2 | 8/2014 | Hoyme et al. | |
| 9,509,507 B1 * | 11/2016 | Hunt | ..................... H04L 9/0883 |
| 2007/0002821 A1 | 1/2007 | Carlson et al. | |
| 2007/0061460 A1 * | 3/2007 | Khan | ...................... H04L 41/00 709/225 |
| 2009/0063187 A1 | 3/2009 | Johnson et al. | |
| 2009/0097623 A1 * | 4/2009 | Bharadwaj | ........... H04M 11/027 379/106.02 |
| 2009/0276013 A1 * | 11/2009 | Matos | ..................... G06Q 50/22 607/60 |
| 2010/0183153 A1 * | 7/2010 | Cho | ....................... H04L 45/122 380/277 |
| 2011/0191767 A1 | 8/2011 | Pinsky et al. | |
| 2012/0026899 A1 | 2/2012 | Lee et al. | |
| 2013/0196703 A1 | 8/2013 | Masoud et al. | |
| 2014/0062718 A1 | 3/2014 | Lalonde et al. | |
| 2014/0086065 A1 | 3/2014 | Decusatis et al. | |
| 2014/0278548 A1 * | 9/2014 | Munro | ................ G06F 19/3418 705/3 |
| 2015/0089590 A1 * | 3/2015 | Krishnan | ................ H04L 63/08 726/3 |
| 2015/0134359 A1 * | 5/2015 | Moskal | ................. G06F 19/322 705/3 |
| 2015/0249921 A1 * | 9/2015 | Lv | ....................... H04L 63/0884 726/4 |
| 2015/0381571 A1 * | 12/2015 | Plasse | ..................... H04L 51/00 726/26 |
| 2016/0119293 A1 * | 4/2016 | Leon | ......................... H04L 9/14 713/168 |

FOREIGN PATENT DOCUMENTS

WO 2013036842 A2 3/2013

OTHER PUBLICATIONS

Yetisen A.K., et al., "The Regulation of Mobile Medical Applications," The Royal Society of Chemistry, 2014, 8 pages.
International Search Report and Written Opinion—PCT/US2016/034322—ISA/EPO—Jul. 21, 2016.

\* cited by examiner

*Primary Examiner* — Brian Whipple
(74) *Attorney, Agent, or Firm* — The Marbury Law Group, PLLC

(57) ABSTRACT

Various embodiments include methods implemented on a server for determining a network transmission path for medical data. The methods may include receiving a request from a requesting node to transmit medical data to a destination node, determining a list of qualified nodes for use in establishing a network for transmitting the medical data to the destination node, and determining at least one transmission path from the requesting node to the destination node using the list of qualified nodes. The method may further include deputizing each node in the at least one transmission path by sending each node in the at least one transmission path credentials that configure each node in the at least one transmission path to communicate the medical data according to a communications standard, and instructing the requesting node to transmit the medical data through the transmission path.

28 Claims, 30 Drawing Sheets

| Credentials |
|---|
| Patient ID |
| Provider ID |
| Destination Node |
| Next Node |
| Previous Node |
| Classification |
| Priority |
| Severity |
| Channel ID |
| Channel Status |

SYSTEMS AND METHODS FOR INCORPORATING DEVICES INTO A MEDICAL DATA NETWORK

BACKGROUND

Patients may be monitored by a host of medical devices from simple scales providing patient weight information to sophisticated electrocardiographs ("EKG") detecting life threatening arrhythmias. These devices generally digitize some aspect of the patient's physiology, converting it into data that can be transmitted to a destination through a wireless communication network. The air interface protocols used in these wireless communication networks are generally short range air interfaces (e.g., Wi-Fi®, Bluetooth®, Bluetooth Low Energy® connections) or cellular/wide area air interfaces (e.g., Third Generation (3G), Fourth Generation (4G), Long Term Evolution (LTE), Time Division Multiple Access (TDMA), Code Division Multiple Access (CDMA), Wideband CDMA (WCDMA), Global System for Mobile Communications (GSM), and Universal Mobile Telecommunications Systems (UMTS), and other mobile telephony communication technologies).

The transmission of medical data over air interfaces may be governed by a number of communications standards promulgated by health regulatory authorities, such as the US Food and Drug Administration (FDA), European Commission Directorate General for Health and Consumers, etc. While specialized medical devices, such as patient monitors, surgical monitors, or specialized hospital devices may be designed to comply with regulatory standards, other more general computing devices may not be configured to comply with the regulatory standards. Such general computing devices may include desktop computers, laptops, tablets, and smart phones. Thus, general computing devices which would otherwise be capable of receiving and transmitting medical data may not be able to participate in regulated medical data networks. In order to participate in such networks, general computing devices may have to be specifically configured to comply with regulatory standards, which reduces the flexibility and increases the cost of setting up medical data networks.

SUMMARY

Various embodiments include methods implemented on a server for determining a network transmission path for medical data. Various embodiment methods that may be implemented on a server may include receiving a request from a requesting node to transmit medical data to a destination node, determining a list of nodes qualified ("qualified nodes") for use in establishing a network for transmitting the medical data to the destination node, determining at least one transmission path from the requesting node to the destination node using the list of qualified nodes, deputizing each node in the at least one transmission path by sending each node in the at least one transmission path credentials that configure each node in the at least one transmission path to communicate the medical data according to a communications standard, and instructing the requesting node to transmit the medical data through the transmission path.

Some embodiments may further include verifying whether the requesting node is qualified to receive or transmit medical data and ignoring the request from the requesting node in response to determining that the requesting node is not qualified to receive or transmit medical data. In some embodiments, determining the list of qualified nodes for use in establishing a network for transmitting the medical data to the destination node may further include receiving communication characteristics of each node, determining whether each node is qualified to transmit the medical data based on communication characteristics of the node and the communications standard, and adding the node to the list of qualified nodes in response to determining that the node is qualified to transmit the medical data. In such embodiments, the communication characteristics may include at least one of a data reception rate, a data transmission rate, a communication interface type, a device type, a communications range, a device identifier, a medium access control address, an interface requirement, a bandwidth capability, a packet redundancy level, a quality of service level, a latency level, a security capability, a link redundancy level, and a power level.

In some embodiments, the credentials may include at least one of a regulatory classification, a priority, a patient identifier, a provider identifier, a channel identifier, a channel status, the at least one transmission path, an identity of a previous node in the at least one transmission path, and an identity of a next node in the at least one transmission path. Some embodiments may further include de-deputizing each node in the at least one transmission path when transmission of the medical data is complete, in which de-deputizing each node may include disabling the credentials on each node.

Some embodiments may further include receiving a request from an intermediate node in the at least one transmission path to change the at least one transmission path, determining at least one alternate transmission path from the requesting node to the destination node using the list of qualified nodes, deputizing each node in the at least one alternate transmission path by sending each node in the at least one alternate transmission path credentials that configure each node in the at least one alternate transmission path to communicate the medical data according to the communications standard, and instructing the requesting node and the intermediate node to transmit the medical data through the at least one alternate transmission path. In some embodiments, the communications standard may be a medical regulatory standard.

Some embodiments may further include determining whether a plurality of transmission paths share a common node, determining whether the common node is capable of supporting the plurality of transmission paths in response to determining that the plurality of transmission paths share the common node, and selecting one or more transmission paths in the plurality of transmission paths for the common node to support in response to determining that the common node is not capable of supporting the plurality of transmission paths. In some embodiments, determining at least one transmission path from the requesting node to the destination node using the list of qualified nodes may include determining at least one of a total transmission distance, available resources of each node in the at least one transmission path, a number of nodes in the at least one transmission path, and a characteristic of the medical data.

Various embodiments include methods implemented on a node for transmitting medical data in the network. Such embodiment methods that may be implemented in a processor of the node may include implementing credentials that configure the node to communicate medical data through a transmission path according to a communications standard, and transmitting the medical data received from a previous node in the transmission path to a next node in the transmission path according to the communications standard.

Some embodiments may further include determining whether a topology of the network has changed or whether the next node is able to receive the medical data, and determining an alternate transmission path in response to determining that the topology of the network has changed or that the next node is not able to receive the medical data. In some embodiments, the node may receive the credentials from a server in response to sending communication characteristics of the node to the server. In such embodiments, the communication characteristics may include at least one of a data reception rate, a data transmission rate, a communication interface type, a device type, a communications range, a device identifier, a medium access control address, an interface requirement, a bandwidth capability, a packet redundancy level, a quality of service level, a latency level, a security capability, a link redundancy level, and a power level.

In some embodiments, the credentials may include at least one of a regulatory classification, a priority, a patient identifier, a provider identifier, a channel identifier, a channel status, the transmission path, an identity of the previous node in the transmission path, and an identity of the next node in the transmission path. In some embodiments, the communications standard may be a medical regulatory standard.

Further embodiments include a server including a processor configured with processor-executable instructions to perform operations of the embodiment methods described above. Further embodiments include a node including a processor configured with processor-executable instructions to perform operations of the embodiment methods described above.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the disclosed embodiments.

DETAILED DESCRIPTION

Figure 1:
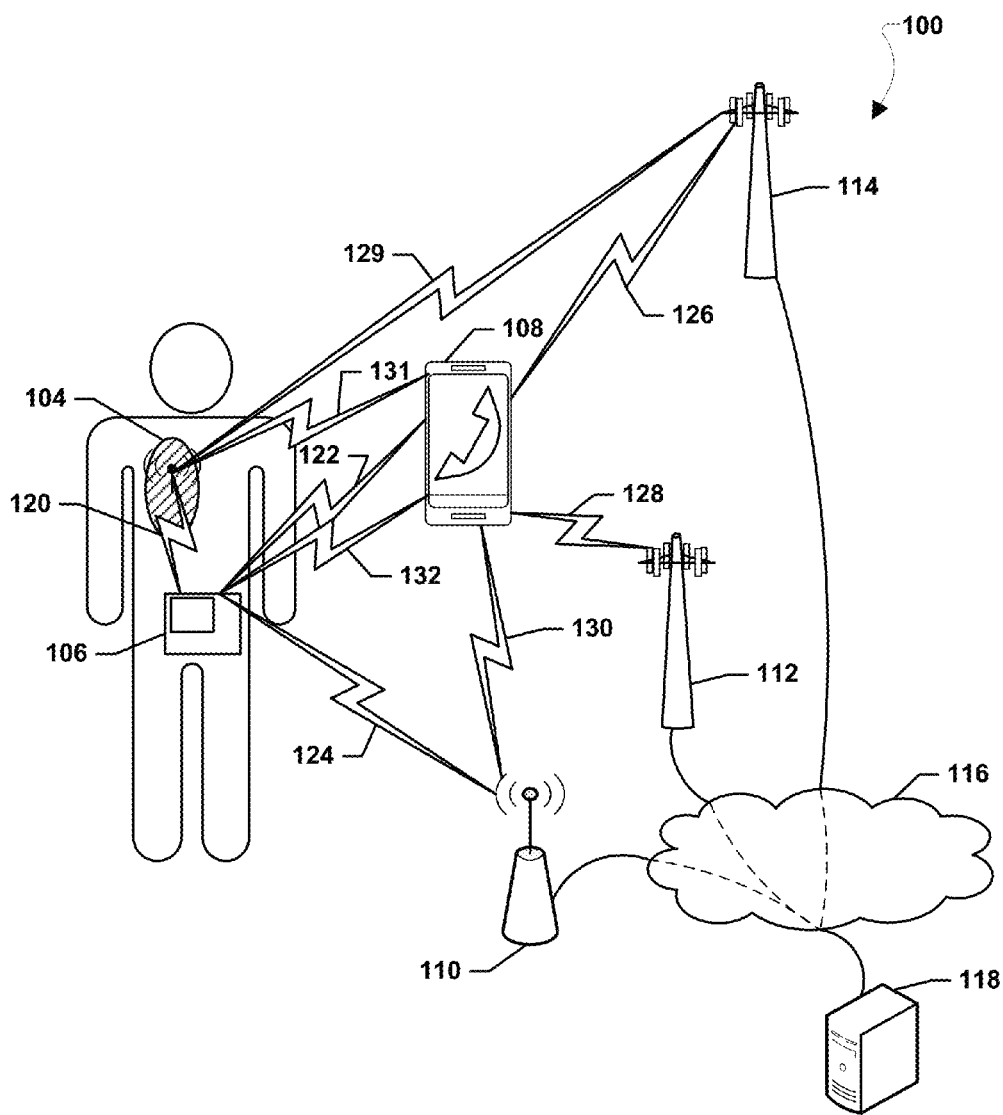
FIG. 1 is a communication system block diagram of a network suitable for use with the various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the various embodiments or the claims.

The word "exemplary" is used herein to mean "serving as an example, instance, or illustration." Any implementation described herein as "exemplary" is not necessarily to be construed as preferred or advantageous over other implementations.

As used herein, the terms "communication device," "computing device," "general computing device," and "mobile device" are used herein to refer to any one or all of cellular telephones, smart phones, personal or mobile multi-media players, personal data assistants (PDA's), laptop computers, tablet computers, desktop computers, smart books, palm-top computers, wireless electronic mail receivers, multimedia Internet enabled cellular telephones, and similar personal electronic devices which include a programmable processor and memory and circuitry for establishing an air interface.

As used herein, the term "medical device" is used to refer to any device that includes a programmable processor and memory and circuitry that may generate, process or relay medical data.

As used herein, the term "base station" is used to refer to any one or all of a cellular tower, hot spot, access point, or similar device which includes a programmable processor and memory and circuitry for establishing an air interface and acting as a gateway between wireless devices and a wired network, such as the Internet.

Health regulatory authorities, such as the U.S. Food and Drug Administration (FDA), European Commission Directorate General for Health and Consumers, etc., set safety and effectiveness requirements for medical devices falling under their regulatory authority. As an example, the FDA classifies medical devices into three regulatory classes, Class I, Class II, and Class III, based on the safety and effectiveness of the medical device as well as the intended use of the medical device, indications of use for the medical device, and risk in use of the medical device. FDA assigned Class I medical devices generally pose the lowest level risk to patient health, Class II medical devices pose a higher level of risk, and Class III medical devices pose the highest level of risk to patient health. As another example, the European Commission Directorate General for Health and Consumers classifies medical devices into five general classes, Class I, Class I Sterile, Class I Measure, Class IIa, Class IIb, and Class III, based on the potential hazard the medical device poses to a patient taking into various factors, such as duration of contact with the body, degree of invasiveness, and local versus systemic effect. European Commission Directorate General for Health and Consumers assigned Class I, Class I Sterile, and Class I Measure medical devices generally pose the least hazard to patient health, Class II medical devices pose a higher level of risk with Class IIb medical devices posing a higher level of risk than Class IIa devices, and Class III medical devices pose the highest level of risk.

While the classifications set by health regulatory authorities, such as the FDA, European Commission Directorate General for Health and Consumers, etc. define safety, effectiveness, and risk requirements, the current classifications do not set requirements for the air interfaces used to transmit medical data between devices. Systems and methods for establishing air interfaces for medical data networks that comply with regulatory standards are disclosed in U.S. patent application Ser. No. 14/184,788, filed Feb. 20, 2014 and entitled "Medical Air Interfaces," which is hereby incorporated by reference in its entirety.

In addition to ensuring that air interfaces comply with regulatory standards, a medical data network should also ensure that devices participating in the network also comply with regulatory standards. Medical devices such as patient monitors, surgical monitors, and specialized hospital equipment may already be configured to comply with regulatory standards. However, other general computing devices such as base stations, desktop computers, laptops, tablets, and smart phones are not configured to comply with regulatory standards. Thus, general computing devices are not qualified to participate in a medical data network unless the computing device is specifically configured to comply with regulatory standards. This increases the time and cost of building a medical data network, and reduces the flexibility of the network.

The systems, methods, and devices of the various embodiments enable dynamic creation of transmission paths through nodes that have not been previously qualified for medical data transmissions in order to facilitate dynamically establishing a medical data network. The medical data network may include a number of nodes and a server or controller that is in wireless or wired communication with the nodes. Nodes may be medical devices or general computing devices.

In the various embodiments, the server may receive a request from a requesting node to transmit medical data to a destination node. The medical data may include, but are not limited to, physiological data, a patient identifier, a regulatory classification, and a priority. The server may verify whether the requesting node is qualified to participate in a medical data network. If the requesting node is qualified to participate in the medical data network, the server may determine a list of qualified nodes in the network for transmitting the medical data. Each node in the network may send the communication characteristics of the node to the server. The server may determine whether each node is qualified to transmit the medical data based on the communication characteristics of the node and the medical data to be transmitted, and add the node to the list of qualified nodes if the node is qualified to transmit the medical data. The communication characteristics may include, but are not limited to, device type or identifier, medium access control (MAC) address, a communications range, data transmission rate, data reception rate, regulatory classification, collected medical data, event triggers, interface requirements, bandwidth capability, packet redundancy level, quality of service level, latency level, security capabilities, link redundancy level, and power level.

The server may determine at least one transmission path from the requesting node to the destination node using the list of qualified nodes. The transmission path(s) may be determined based on a number of factors, including total transmission distance, available bandwidth or other resources of each node in list of qualified nodes, the number of nodes used, and the priority of the medical data. The server may "deputize" each node in a transmission path by sending credentials to each node in the transmission path. Such credentials may configure each node to communicate the medical data according to a communications standard. The credentials may allow general computing devices to participate in the medical data network even though the computing devices are not specifically configured or previous qualified for use in a medical data network. The communications standard may be a regulatory standard, such as those promulgated by the FDA or the European Commission Directorate General for Health and Consumers. The credentials may include, but are not limited to, a patient identifier, a provider identifier, the identities of the requesting node, destination node, next node in the transmission path, and the previous node in the transmission path, a regulatory classification, a priority, a severity, a channel identifier, and a channel status. The server may then instruct the requesting node to transmit the medical data through the transmission path.

The server may receive a request from an intermediate node in the transmission path to change the transmission path, such as because the next node in the transmission path is not functioning properly. The server may determine an alternate transmission path from the intermediate node to the destination node using the list of qualified nodes, and may deputize each node in the alternate transmission path by sending each node in the alternate transmission path credentials that configure the node to communicate the medical data according to the communications standard. The server may then instruct the intermediate node to transmit the medical data through the alternate transmission path. Once the transmission of medical data is complete, the server may de-deputize each node in the transmission path by removing the credentials sent to each node.

The server may determine whether a number of transmission paths share a common node in the medical data system. The server may determine whether the common node is capable of supporting all of the transmission paths. If the common node is not capable of supporting all transmission paths, the server may select a subset of the transmission paths for the common node to support. The selection may be based on the priority of various transmission paths, the device capabilities, and available resources of the common node.

Additional systems, methods, and devices of the various embodiments may enable a node to participate in a medical data network communicating medical data. The node may send communication characteristics of the node to a server controlling a medical data network and receive from the server credentials that configure the node to communicate the medical data through a transmission path according to a communications standard. Alternatively, the node may independently implement credentials that configure the node to communicate the medical data. The node may receive the medical data from a previous node in the transmission path according to the communications standard and transmit the medical data to a next node in the transmission path according to the communications standard. When the node has finished transmitting the medical data, the node may disable or delete the credentials.

The node may determine whether a topology of the network has changed, or whether the next node is unable to receive the medical data. In response to either event, the node may send a request to the server for an alternate transmission path. The node may receive from the server an alternate transmission path and transmit the medical data through the alternate transmission path to the destination node. Alternatively, the node may independently determine an alternate transmission path. In this manner, the server and nodes may implement a dynamic medical data network in which medical devices and general computing devices may be assembled into transmission paths for medical data in an ad hoc fashion.

FIG. 1 illustrates a wireless network system 100 suitable for use with the various embodiments. The wireless network system 100 may include multiple medical devices, such as a medical sensor patch 104 and a medical analyzer 106 (e.g., an EKG machine, smart watch, heart rate monitor, activity monitoring band, etc. that may gather and/or analyze medical data), a mobile device, such as a smart phone 108, and base stations, such as cellular tower 114, cellular tower 112, and hot spot 110, and one or more servers 118 connected to a network 116. The cellular tower 114, cellular tower 112, and hot spot 110 may be in communication with routers which may connect to the network 116. In this manner, via the connections to the network 116 the cellular tower 114, cellular tower 112, and hot spot 110 may act as gateways between wireless devices connected to the cellular tower 114, cellular tower 112, or hot spot 110 via air interfaces and the network 116 and connected server 118. The network 116 may be a medical data network, or the Internet, or some other communication network.

Medical sensor patch 104 may be a device including one or more sensors worn by or attached to a user or patient. As examples, the medical sensor patch 104 may be an adhesive patch, a wearable arm band, a wrist watch, a necklace, an article of clothing, or any other type of device including one or more sensors worn by or attached to a user or patient. While a single patient or user is illustrated in FIG. 1 associated with only one medical sensor patch 104, multiple medical sensor patches, with the same or different sensors, may be worn by or attached to one or more users or patients at any given time.

The medical sensor patch 104 may gather, integrate, process, and/or analyze measurements from its different sensors to generate medical data. Different sensors in the medical sensor patch 104 may include various types, e.g., electrical, optical, physical, activity, and chemical sensors, measuring physiological or biological signals of the user or patient. The medical sensor patch 104 may exchange data with the medical analyzer 106 via an air interface 120, such as a short range air interface (e.g., a Bluetooth® or Bluetooth Low Energy (LE)® connection) established between the medical sensor patch 104 and the medical analyzer 106. The medical sensor patch 104 may exchange data with the smart phone 108 via an air interface 131 (e.g., a Bluetooth® or Bluetooth Low Energy (LE)® connection, Wi-Fi® connection, etc.) established between the medical sensor patch 104 and the smart phone 108. The medical sensor patch 104 may exchange data with a base station, such as cellular tower 114, via an air interface 129 (e.g., 3G, 4G, LTE, TDMA, CDMMA, WCDMA, GSM, UMTS, and other mobile telephony communication technologies) established between the medical sensor patch 104 and the base station. The medical sensor path 104 may exchange data with the server 118 through one of the base stations 110, 112, 114 and the network 116.

The medical analyzer 106 may exchange data with the hot spot 110 via an air interface 124 (e.g., a Wi-Fi® connection) established between the hot spot 110 and medical analyzer 106. The medical analyzer 106 may exchange data with the smart phone 108 via an air interface 122 (e.g., a Wi-Fi® connection) established between the smart phone 108 and the medical analyzer 106 or via a different air interface 132 (e.g., a Bluetooth® connection) established between the smart phone 108 and the medical analyzer 106. While not illustrated in FIG. 1, the medical analyzer 106 may also exchange data with a base station, such as cellular towers 112, 114, via an air interface (e.g. 3G, 4G, LTE, TDMA, CDMMA, WCDMA, GSM, UMTS, and other mobile telephony communication technologies) established between the medical analyzer 106 and the base station. The medical analyzer 106 may exchange data with the server 118 through one of the base stations 110, 112, 114 and the network 116.

The smart phone 108 may exchange data with the cellular tower 114 via an air interface 126 (e.g., 3G, 4G, LTE, TDMA, CDMMA, WCDMA, GSM, UMTS, and other mobile telephony communication technologies) established between the smart phone 108 and cellular tower 114. The smart phone 108 may exchange data with the cellular tower 112 via an air interface 128 (e.g., 3G, 4G, LTE, TDMA, CDMMA, WCDMA, GSM, UMTS, and other mobile telephony communication technologies) established between the smart phone 108 and cellular tower 112. The smart phone 108 may exchange data with the hot spot 110 via an air interface 124 (e.g., a Wi-Fi® connection) established between the smart phone 108 and hot spot 110. The smart phone 108 may exchange data with the server 118 through one of the base stations 110, 112, 114 and the network 116.

The server 118 may include one or more servers or controllers for storing medical data received from the medical sensor patch 104, the medical analyzer 106, and the smart phone 108. The server 118 may also implement a dynamic medical data network such as the network 116, with the medical sensor patch 104, the medical analyzer 106, and the smart phone 108 functioning as nodes within the network. The server 118 may also be in communication with various other nodes not illustrated in FIG. 1. The server 118 may be configured to receive requests to transmit medical data between nodes, identify transmission paths for the medical data from a list of qualified nodes, and deputize nodes to participate in the medical data network to transmit the medical data.

Figure 2A:
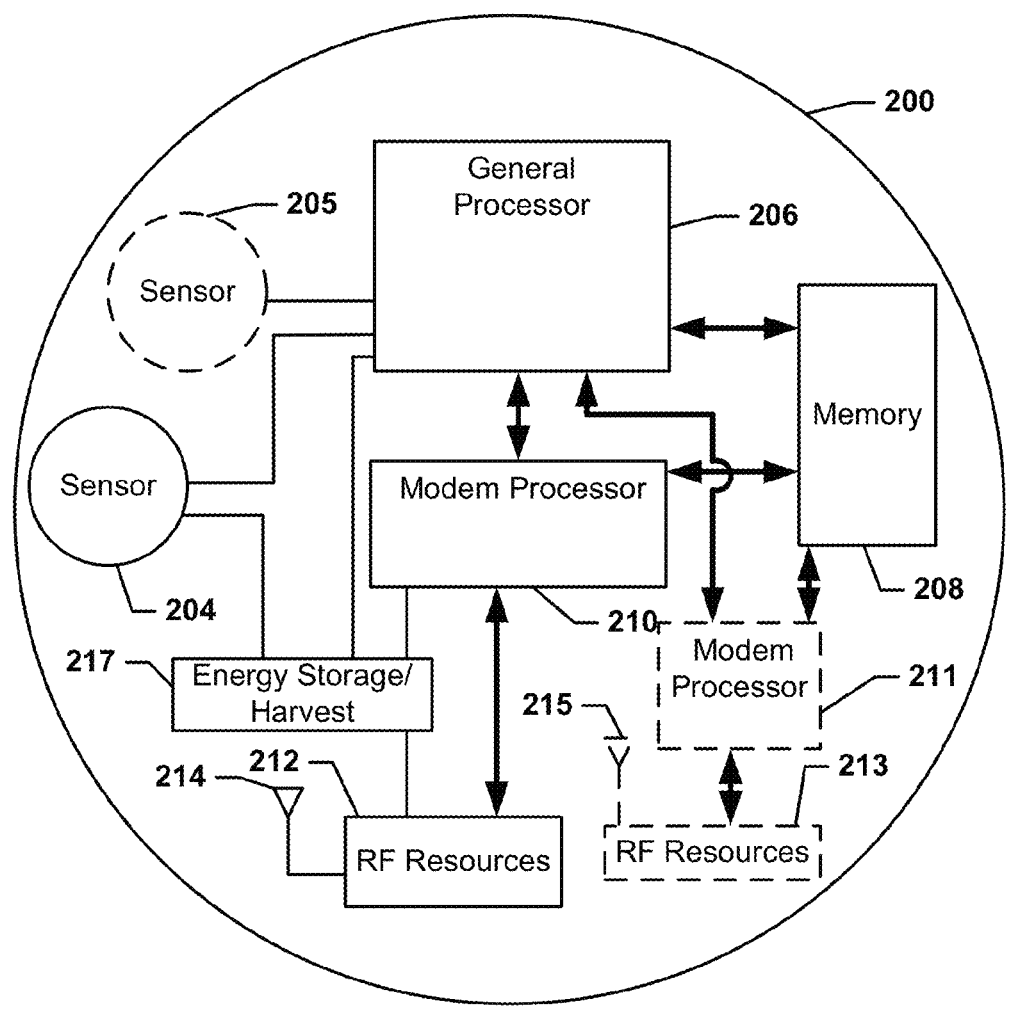
FIG. 2A is a component block diagram illustrating a wireless medical device according to an embodiment.

FIG. 2A is a component block diagram illustrating a medical wireless on-patient sensing device 200, such as a medical sensor patch according to an embodiment. The wireless on-patient sensing device 200 may include one or more controllers, such as a general purpose processor 206, which may be coupled to at least one sensor 204, such as an EKG lead, temperature sensor, etc. and optionally additional sensors 205, such as activity sensors, chemical sensors, air quality sensors, etc. The sensors 204 and 205 may be the same type of sensors (e.g., both EKG leads) or different types of sensors (e.g., a temperature sensor and a blood glucose sensor). The sensors 204 and 205 may monitor some aspect of a patient's physiology and output data to the general purpose processor 206. The general purpose processor 206 may also be coupled to at least one memory 208. The memory 208 may be a non-transitory processor-readable medium storing processor-executable instructions and other data, including communication characteristics of the wireless on-patient sensing device 200 and credentials sent by a server in a medical data network.

The memory 208 and the general purpose processor 206 may each be coupled to at least one modem processor 210, which may be coupled to various radio frequency (RF) resources 212 including one or more amplifiers, radios, power sources, etc. Optionally, the memory 208 and general purpose processor 206 may be coupled to one or more additional modem processors 211, which may be coupled to various RF resources 213 including one or more amplifiers, radios, power sources, etc. The RF resources 212 and 213 may be coupled to antennas 214 and 215, respectively. Together the modem processor 210, the RF resources 212, and antenna 214 may include an RF resource chain that may perform transmit/receive functions for the wireless on-patient sensing device 200. As examples, the RF resource chain may be a Bluetooth®, Wi-Fi®, or cellular/wide area resource chain enabling the wireless on-patient sensing device 200 to establish air interfaces using Bluetooth®, Wi-Fi®, or cellular/wide area connections to other devices.

The modem processor 211, the RF resources 213, and antenna 215 may include another RF resource chain that may perform transmit/receive functions for the wireless on-patient sensing device 200. The RF resource chains of the wireless on-patient sensing device may be the same type of RF resource chains (e.g., both short range (e.g., Bluetooth®) resource chains) or different types of resource chains (e.g., one Wi-Fi® resource chain and one 3G resource chain).

In an embodiment, the general purpose processor 206 may be configured with processor-executable instructions to perform operations for participating as a node in a medical data network. In an embodiment, the wireless on-patient sensing device 200 may include one or more energy storage/harvesting system 217, such as a battery or solar cell, to output electrical energy for use by connected hardware, such as the general purpose processor 206, modem processor 210, RF resources 212, and sensor 204, or any other hardware included in the wireless on-patient sensing device 200.

Figure 2B:
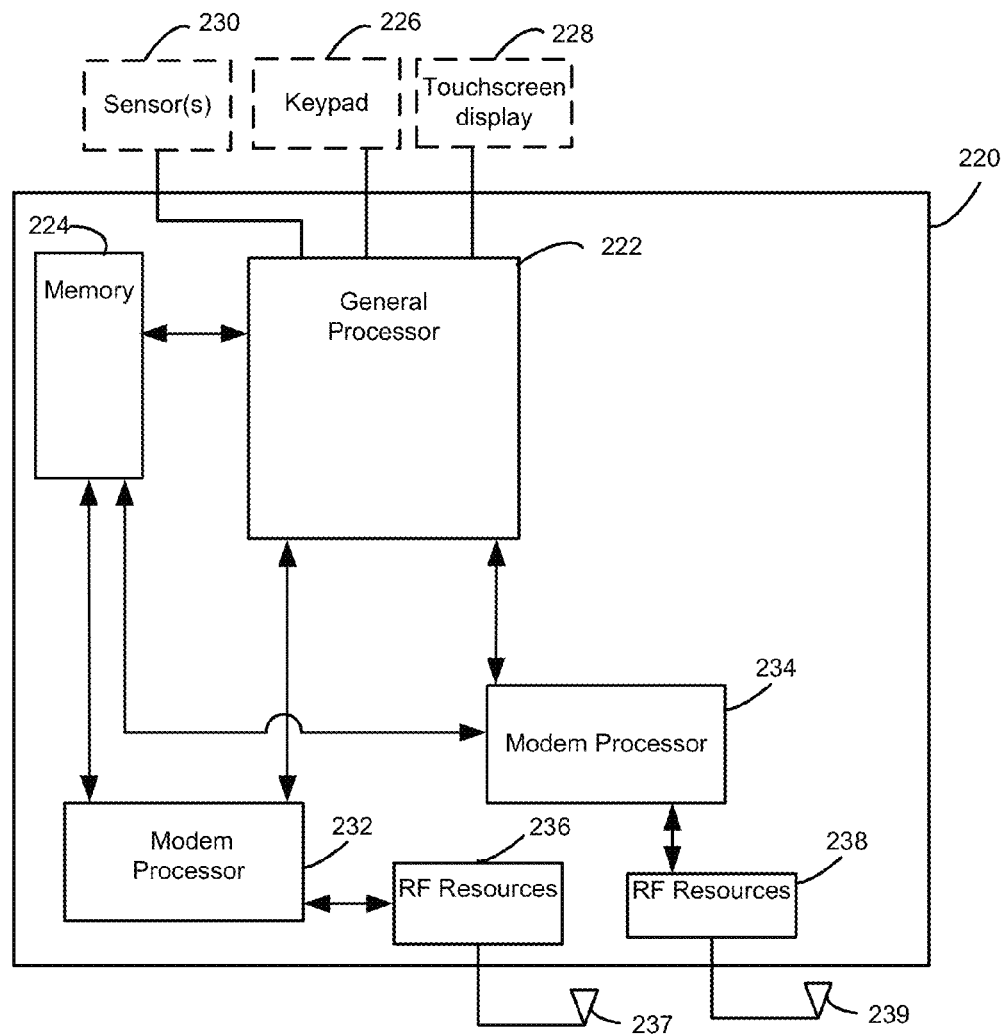
FIG. 2B is a component block diagram illustrating another wireless medical device according to an embodiment.

FIG. 2B is a component block diagram illustrating a medical analyzer 220, such as an EKG, smart watch, fitness band, etc., according to an embodiment. The medical analyzer 220 may include one or more controllers, such as a general purpose processor 222, which may be coupled to one or more optional sensors 230 (e.g., an EKG lead, weight scale, thermometer, etc.), an optional keypad 226, and an optional touchscreen display 228. The sensor(s) 230 may monitor some aspect of a patient's physiology and output data to the general purpose processor 222. The keypad 226 and touchscreen display 228 may receive inputs from a user of the medical analyzer 220 and output indications of the inputs to the general purpose processor 222. The general purpose processor 222 may also be coupled to at least one memory 224. Memory 224 may be a non-transitory processor-readable medium storing processor-executable instructions and other data, including communication characteristics of the medical analyzer 220 and credentials sent by a server in a medical data network.

The memory 224 and the general purpose processor 222 may each be coupled to two different modem processors 232 and 234. The modem processors 232 and 234 may be coupled to various RF resources 236 including one or more amplifiers, radios, power sources, etc. The RF resources 236 may be coupled to an antenna 237. Together the modem processor 232, the RF resources 236, and antenna 237 may constitute a first RF resource chain that may perform transmit/receive functions for the medical analyzer 220. For example, the first RF resource chain may be a Bluetooth® resource chain enabling the medical analyzer 220 to establish air interfaces using Bluetooth® connections to other devices, such as the wireless on-patient sensing device 200 described above, to transmit/receive medical data. The modem processor 234 may be coupled to various RF resources 238, including one or more amplifiers, radios, power sources, etc. The RF resources 238 may be coupled to an antenna 239. Together the modem processor 234, the RF resources 238, and antenna 239 may constitute a second RF resource chain that may perform transmit/receive functions for the medical analyzer 220 different from the first RF resource chain. For example, the second RF resource chain may be a Wi-Fi® resource chain enabling the medical analyzer 220 to establish air interfaces using Wi-Fi® connections to other devices to transmit/receive medical data. In an embodiment, the general purpose processor 222 may be configured with processor-executable instructions to perform operations for participating as a node in a medical data network.

Figure 2C:
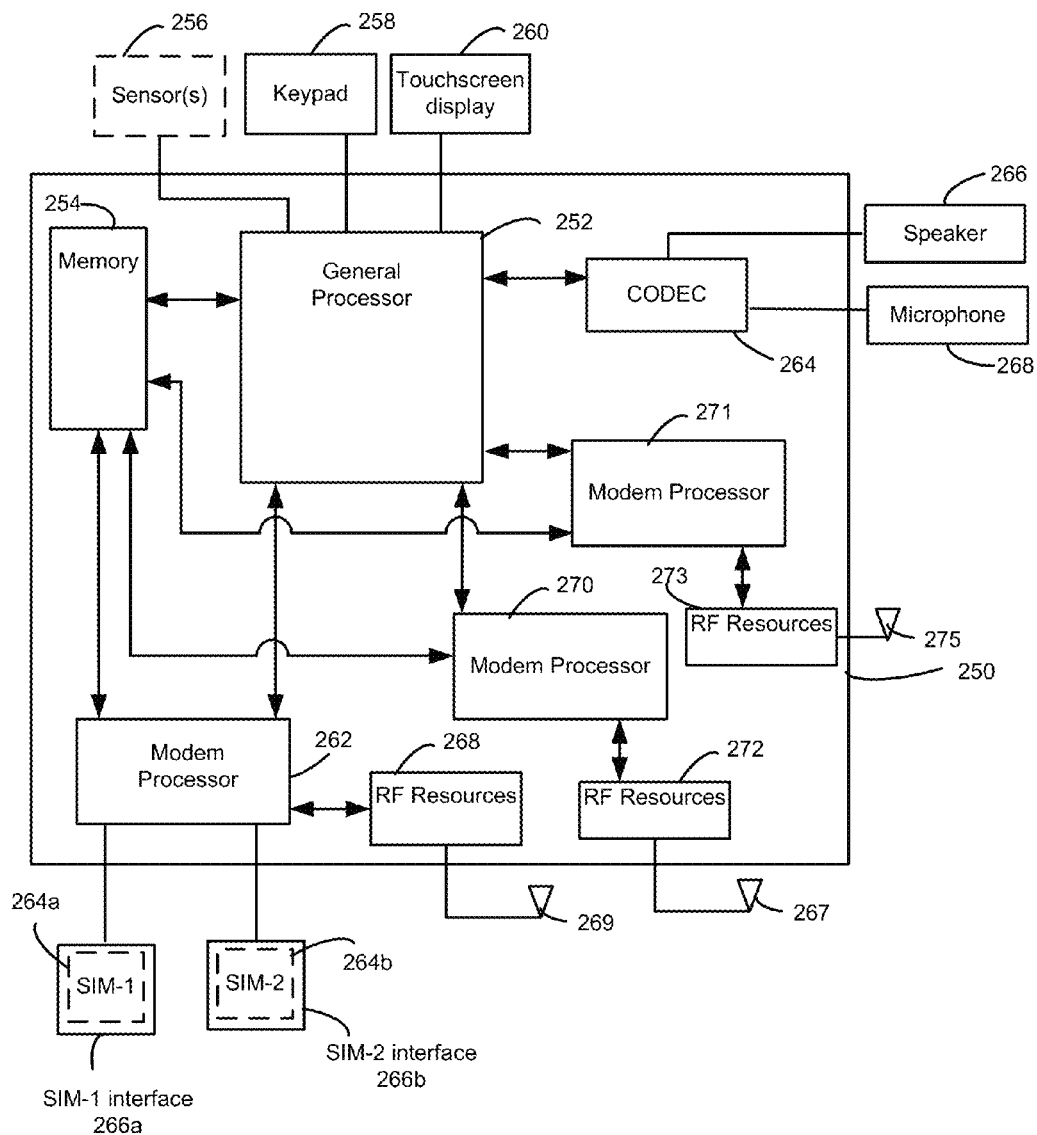
FIG. 2C is a component block diagram illustrating a mobile device according to an embodiment.

FIG. 2C is a component block diagram illustrating a general mobile device 250, such as a smart phone, according to an embodiment. The mobile device 250 may include one or more controllers, such as a general purpose processor 252, which may be coupled to one or more optional sensors 256, such as a pulse monitor, weight scale, thermometer, pedometer etc., a keypad 258, and a touchscreen display 260. The sensor(s) 256 may monitor some aspect of a patient's physiology and output data to the general purpose processor 252. The keypad 258 and touchscreen display 260 may receive inputs from a user of the mobile device 250 and output indications of the inputs to the general purpose processor 252. The general purpose processor 252 may also be coupled to at least one memory 254. Memory 254 may be a non-transitory processor-readable medium storing processor-executable instructions and other data, including communication characteristics of the mobile device 250 and credentials sent by a server in a medical data network.

The mobile device 250 may include a coder/decoder (CODEC) 264 coupled to the general purpose processor 252. The CODEC 264 may in turn be coupled to a speaker 266 and a microphone 268.

The memory 254 and general purpose processor 252 may each be coupled to two or more different modem processors 270 and 271. The modem processor 270 may be coupled to various RF resources 272 including one or more amplifiers, radios, power sources, etc. The RF resources 272 may be coupled to an antenna 267. Together the modem processor 270, the RF resources 272, and antenna 267 may constitute a first RF resource chain that may perform transmit/receive functions for the mobile device 250. For example, the first RF resource chain may be a Bluetooth® resource chain enabling the mobile device 250 to establish air interfaces using Bluetooth® connections to other devices, such as the medical analyzer 220 described above, to transmit/receive medical data. The modem processor 271 may be coupled to various RF resources 273 including one or more amplifiers, radios, power sources, etc. The RF resources 273 may be coupled to an antenna 275. Together the modem processor 271, the RF resources 273, and antenna 275 may constitute a second RF resource chain that may perform transmit/receive functions for the mobile device 250 different from the first RF resource chain. For example, the second RF resource chain may be a Wi-Fi® resource chain enabling the mobile device 250 to establish air interfaces using Wi-Fi® connections to other devices, such as a Wi-Fi® hot spot, to transmit/receive medical data.

In an embodiment, the mobile device 250 may be a multi-subscriber identity module (multi-SIM) device and may include multiple SIM interfaces 266a and 266b which may each receive its own identity module SIM-1 264a and SIM-2 264b each associated with a different cellular subscription. Each SIM may have a central processing unit (CPU), read-only memory (ROM), random access memory (RAM), electrically erasable programmable read-only memory (EEPROM), and input/output (I/O) circuits and may include information identifying a subscriber device to a network. The general purpose processor 252 and the memory 254 may be coupled to at least one modem processor 262, such as a baseband modem processor, that may be coupled to the SIM interfaces 266a and 266b as well as the RF resources 268 including one or more amplifiers, radios, power sources, etc., connected to the antenna 269. Together the modem processor 262, RF resources 268, and antenna 269 may constitute a third RF resource chain that may perform transmit/receive functions for the mobile device 250 different from the first and second RF resource chain. While illustrated as multiple SIMs sharing a single RF resource chain, in another embodiment each SIM-1 264a and SIM-2 264b may have its own separate resource chain. In an embodiment, the general purpose processor 252 may be configured with processor-executable instructions to perform operations for participating as a node in a medical data network.

Figure 2D:
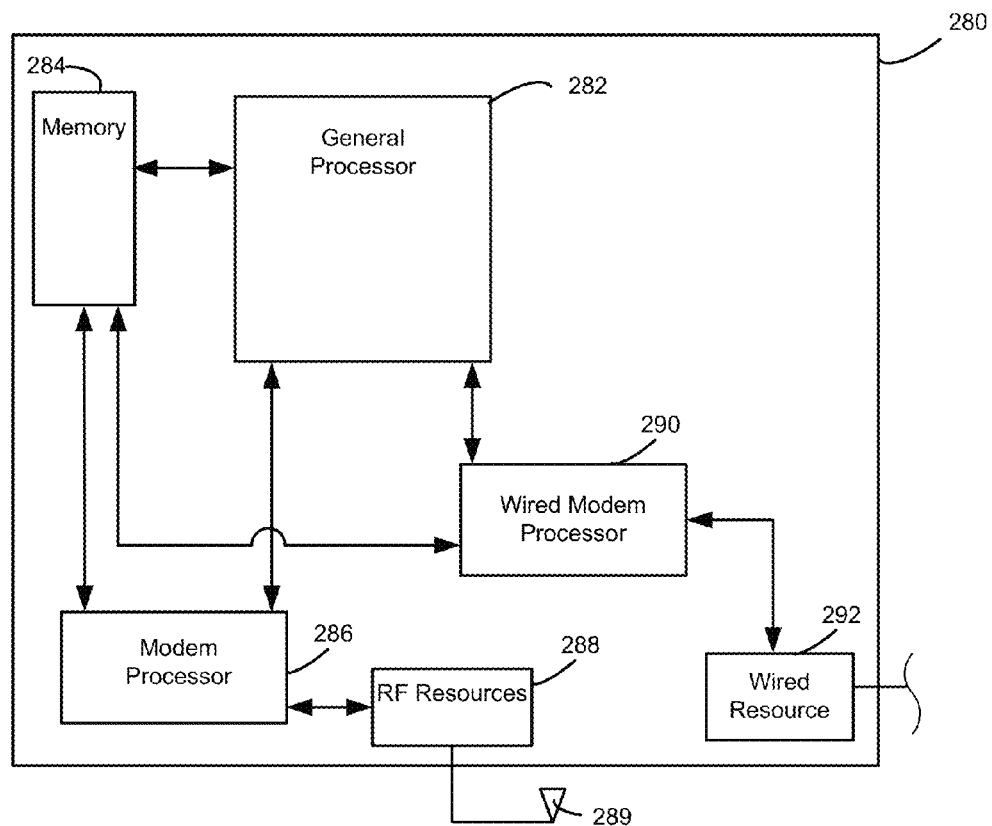
FIG. 2D is a component block diagram illustrating a server according to an embodiment.

FIG. 2D is a component block diagram illustrating a server 280, such as a medical provider computer for overseeing a medical data network, according to an embodiment. The server 280 may include one or more controllers, such as a general purpose processor 282, which may be coupled to at least one memory 284. Memory 284 may be a non-transitory processor-readable medium storing processor-executable instructions and other data, including the identities and communication characteristics of nodes within the medical data network, the topology of the medical data network, and credentials to send to nodes in the medical data network.

The memory 284 and general purpose processor 282 may each be coupled to at least one modem processor 286, such as a short range modem processor or baseband modem processor, that may be coupled to the RF resources 288 including one or more amplifiers, radios, power sources, etc., connected to the antenna 289. Together the modem processor 286, RF resources 288, and antenna 289 may constitute an RF resource chain that may perform transmit/receive functions for the server 280. Additionally or alternatively, the memory 284 and general purpose processor 282 may be coupled to at least one wired modem processor 290 coupled to a wired resource 292 connected to a wired network, such as the Internet or a medical data network. In an embodiment, the general purpose processor 282 may be configured with processor-executable instructions to perform operations for establishing a dynamic medical data network using a number of nodes in communication with the server 280.

Figure 3:
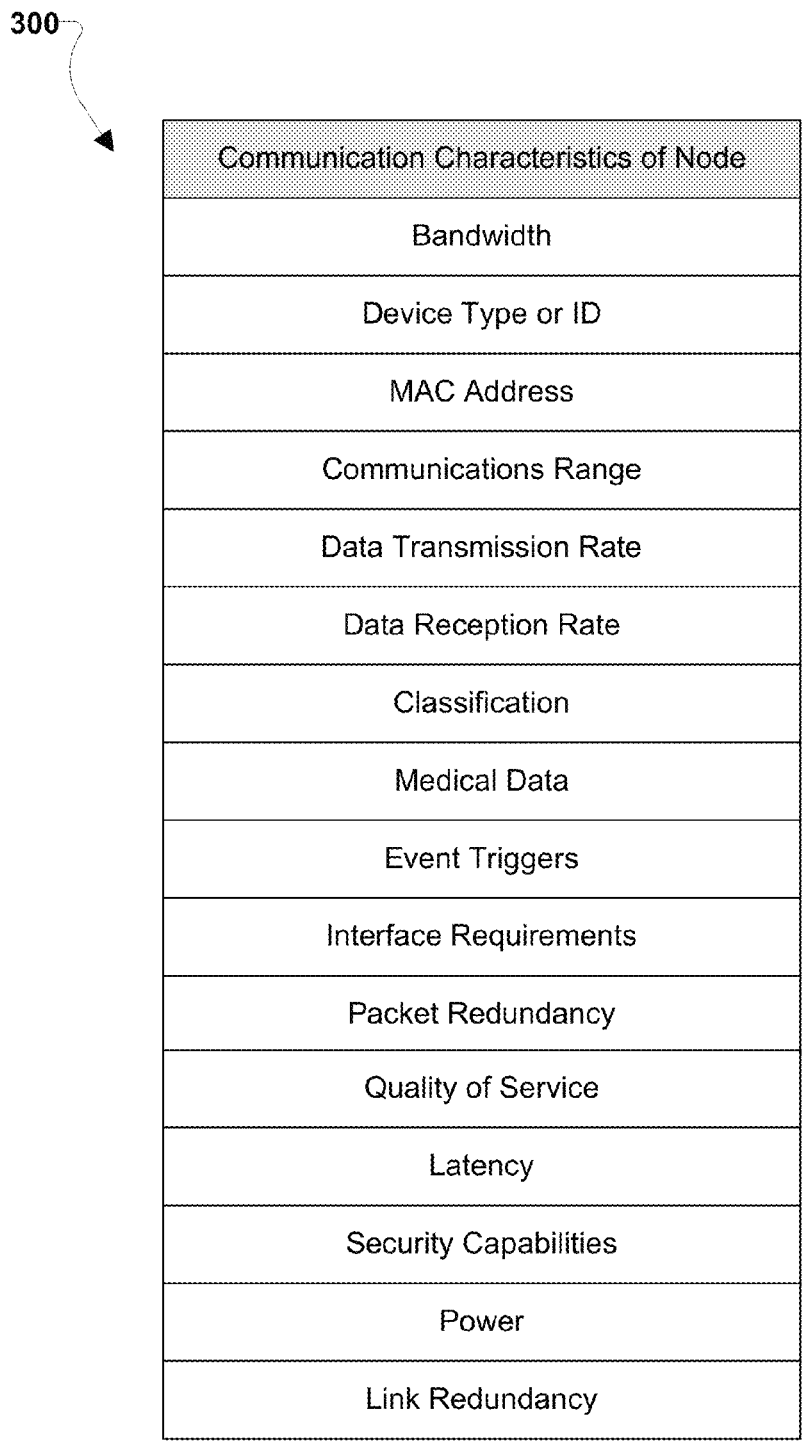
FIG. 3 is a diagram illustrating example communication characteristics of nodes in accordance with various embodiments.

FIG. 3 illustrates examples of communication characteristics 300 of a node in a medical data network. The node may be a medical device or a general computing device, such as wireless on-patient sensing device 200, medical analyzer 220, mobile device 250, and base stations 110, 112, and 114. The communication characteristics 300 may be transmitted by a node to a server controlling the medical data network either upon request of the server, or independently in a periodic or non-periodic manner. The communication characteristics 300 may be used by the server to determine whether the node is qualified to participate in a transmission path for medical data in the medical data network. For example, the medical data to be transmitted may have certain bandwidth or quality of service requirements based on a regulatory classification of the medical data. The server may determine whether the node has the requisite available bandwidth and quality of service levels necessary to transmit the medical data. For example, if the medical data is classified as Class III under FDA regulations, and therefore has a high transmission priority, the server may check the communication characteristics 300 of the node to determine whether the node has sufficient bandwidth and quality of service levels to transmit the medical data quickly and with high reliability.

The communication characteristics 300 may include, but are not limited to, device type or identifier, MAC address, a communications range, data transmission rate, data reception rate, regulatory classification, collected medical data, event triggers, interface requirements, bandwidth capability, packet redundancy level, quality of service level, latency level, security capabilities, link redundancy level, and power level. If the node is also a medical device, additional communication characteristics may include a regulatory classification, collected medical data, and event triggers. Other parameters not listed or shown in FIG. 3 may be included in the communication characteristics 300 and may be utilized by a server to determine whether the node is qualified to transmit medical data in a particular situation.

Figure 4:
FIG. 4 is a diagram illustrating example credentials that allow nodes to participate in medical data networks in accordance with various embodiments.

FIG. 4 illustrates an example of credentials 400 generated by a server controlling a medical data network and sent to a node within the network according to various embodiments. The server may generate the credentials 400 based on the communication characteristics 300 of the node, the medical data being transmitted, and the transmission path for the medical data. The credentials 400 may enable the node to participate in a transmission path for medical data in the medical data network. Without the credentials 400, the node may not be permitted or capable of receiving or transmitting the medical data. The credentials 400 may enable the node to transmit medical data in accordance with a communications standard, such as a medical regulatory standard. The credentials 400 may be stored in memory on the node and may act like a wrapper or abstraction layer between the processor of the node and various resources of the node. For example, the credentials 400 may determine the amount of memory, CPU time, RF bandwidth, or modem cache to reserve for the reception and transmission of medical data. The credentials 400 may also include the topology of the transmission path and required information to be transmitted with the medical data.

The credentials 400 may include, but are not limited to, a patient identifier, a provider identifier, the identity of the requesting node, the identity of the destination node, the identity of the next node in the transmission path, the identity of the previous node in the transmission path, a regulatory classification, a priority, a severity, a channel identifier, and a channel status. Other parameters not listed or shown in FIG. 4 may be included in the credentials 400.

One or more of the credentials 400 may be specific to the medical data being transmitted. In other words, the node may receive credentials 400 for each transmission path in which the node participates, and those credentials cannot be used for another transmission path. The credentials 400 may also be unique to each node in the transmission path such that the credentials 400 for different nodes in the same transmission path are different.

FIGS. 5A-5H illustrate a medical data network 500 capable of dynamic transmission of medical data from one node to another node through the use of credentials according to various embodiments. The medical data network 500 illustrated in FIG. 5A includes one or more servers 502 for controlling the transmission of medical data through the medical data network 500. The medical data network 500 also includes a number of nodes in communication with server 502, such as medical sensors 504 and 514, medical analyzer 506, mobile devices 508 and 510, base station 512, and computing devices 516, 518, and 520 that may relay medical data. The medical data network 500 may include other nodes not illustrated in FIG. 5A.

Figure 5A:
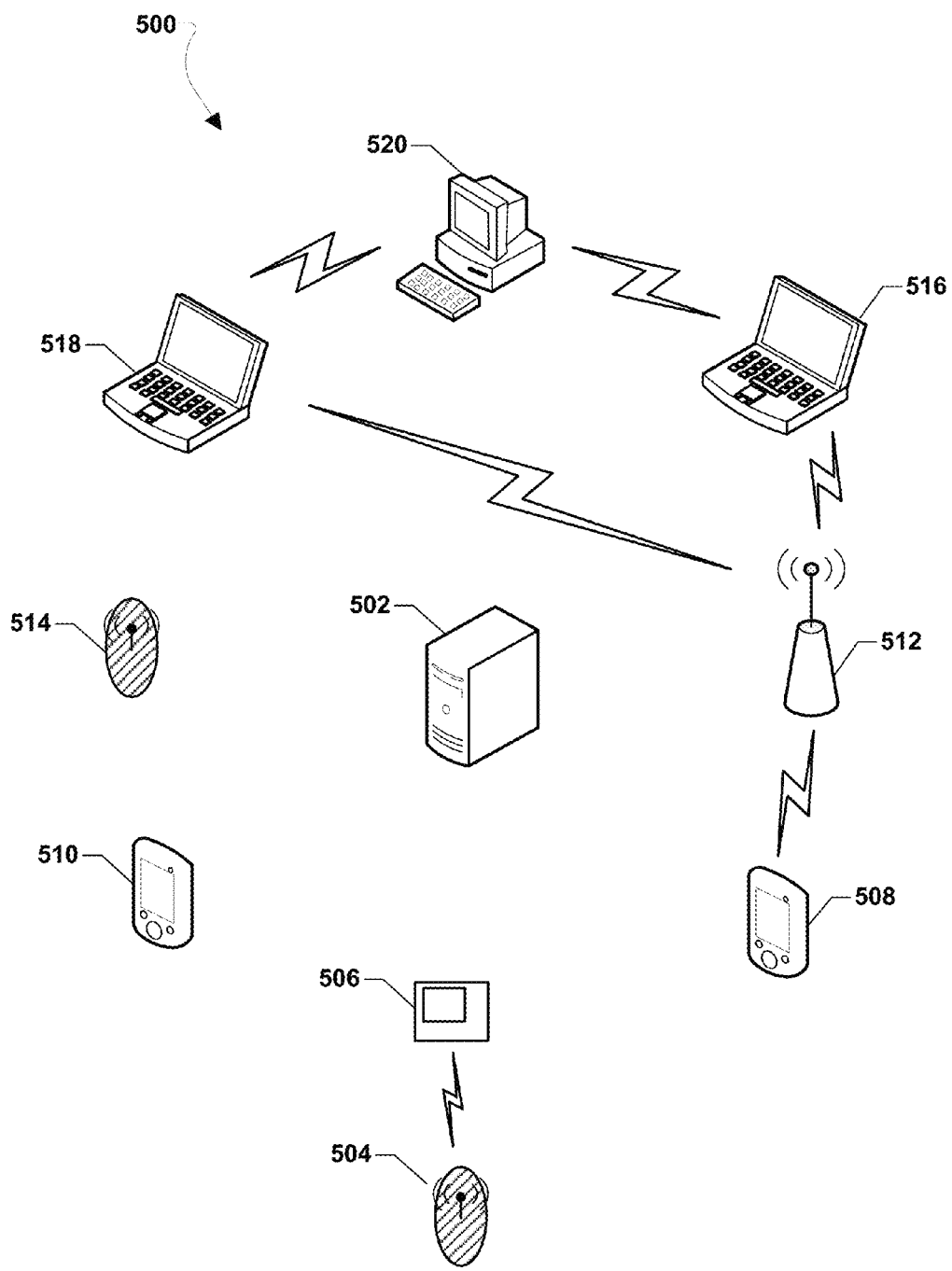
FIGS. 5A-5H illustrate a system for establishing a transmission path in a medical data network in accordance with various embodiments.

In the example illustrated in FIG. 5A, the medical sensor 504 is in communication with a medical analyzer 506, the base station 512, which may be a cellular tower or hotspot, is in communication with mobile device 508 and computing devices 516 and 518, and the computing device 520 is in communication with computing devices 516 and 518. The mobile devices 508, 510, the base station 512, and the computing devices 516, 518, and 520 may be general computing devices in that the devices are not specifically configured to transmit medical data in accordance with a regulatory medical standard. Additionally, the medical devices 504, 506, and 514 may or may not be specifically configured to transmit medical data in accordance with a regulatory medical standard.

Figure 5B:
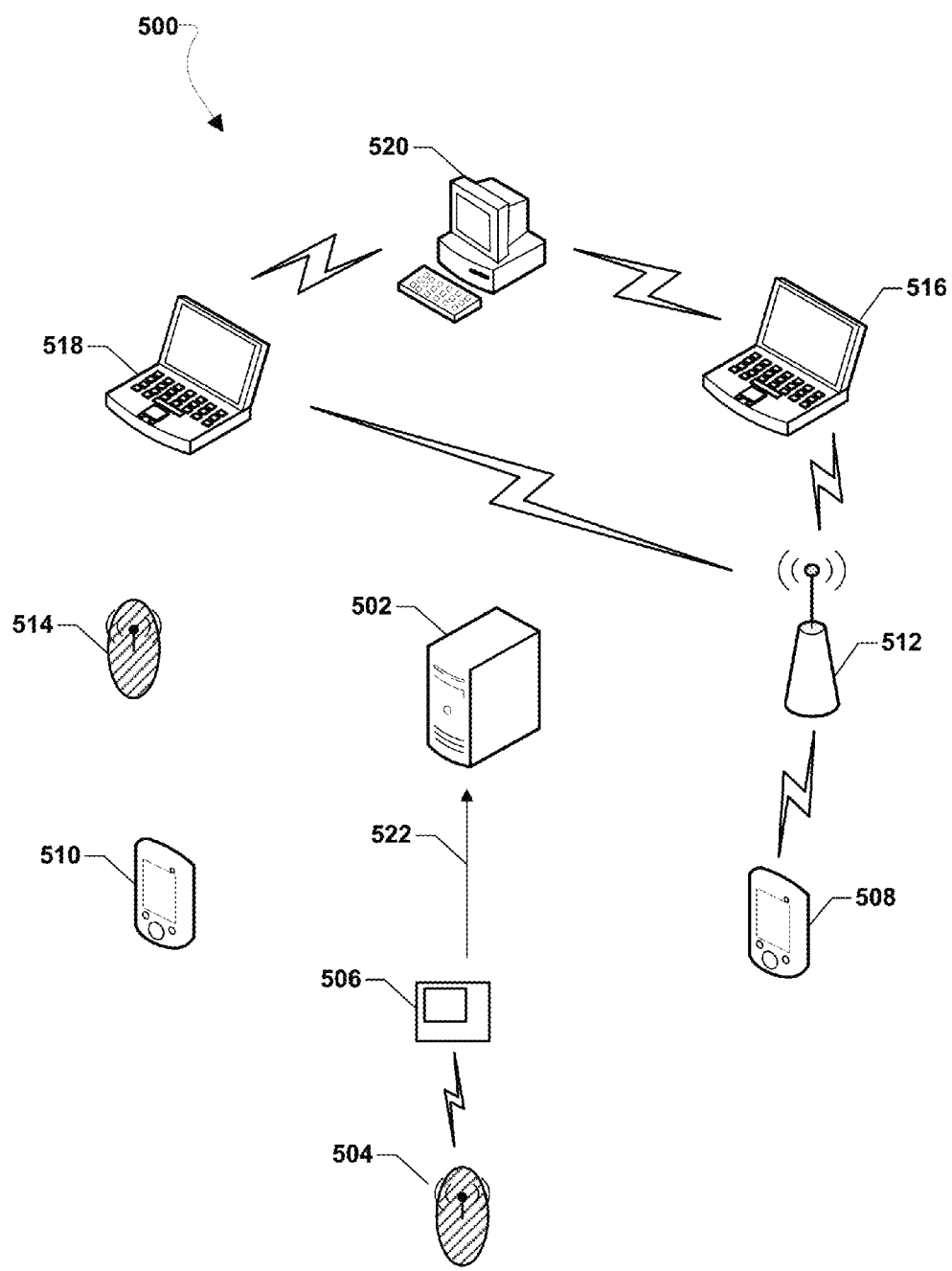

A requesting node in the medical data network 500 may request transmission of medical data to a destination node as illustrated in FIG. 5B. For example, the medical analyzer 506 may receive medical data from the medical sensor 504, which is attached to a patient. The medical data may include, but are not limited to, physiological data, a patient identifier, a regulatory classification, and a priority. The medical analyzer 506 (the requesting node) may send a request 522 to the server 502 to transmit the medical data to the computing device 520 (the destination node), which for example may be a medically staffed monitoring station. The server 502 may verify whether the medical analyzer 506 is qualified to transmit medical data over the medical data network 500, for example by checking permissions. If the medical analyzer 506 is not qualified to transmit medical data over the medical data network 500, the server 502 may ignore the request 522.

Figure 5C:
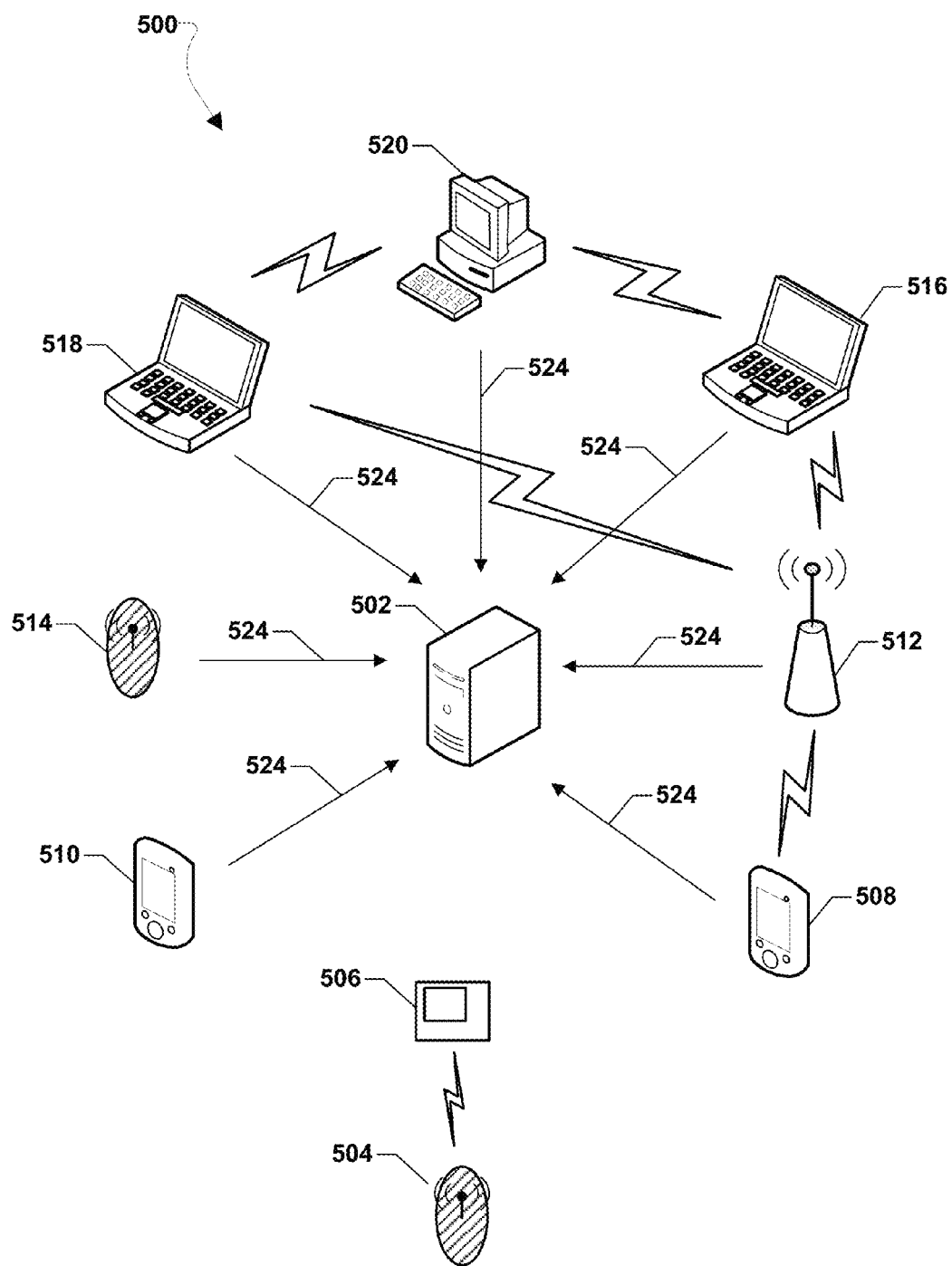

In response to receiving the transmission request 522 from the medical analyzer 506, the server 502 may receive communication characteristics 524 from each node in the medical data network 500 as illustrated in FIG. 5C. The communication characteristics 524 may include one or more of the communication characteristics 300 illustrated in FIG. 3. The server 502 may also receive communication characteristics from the medical analyzer 506 and the medical sensor 504 as well (not illustrated in FIG. 5C). The server 502 may request each node to send the communication characteristics 524 to the server 502, or each node may independently send the communication characteristics 524 to the server 502 on a periodic or non-periodic basis.

Figure 5D:
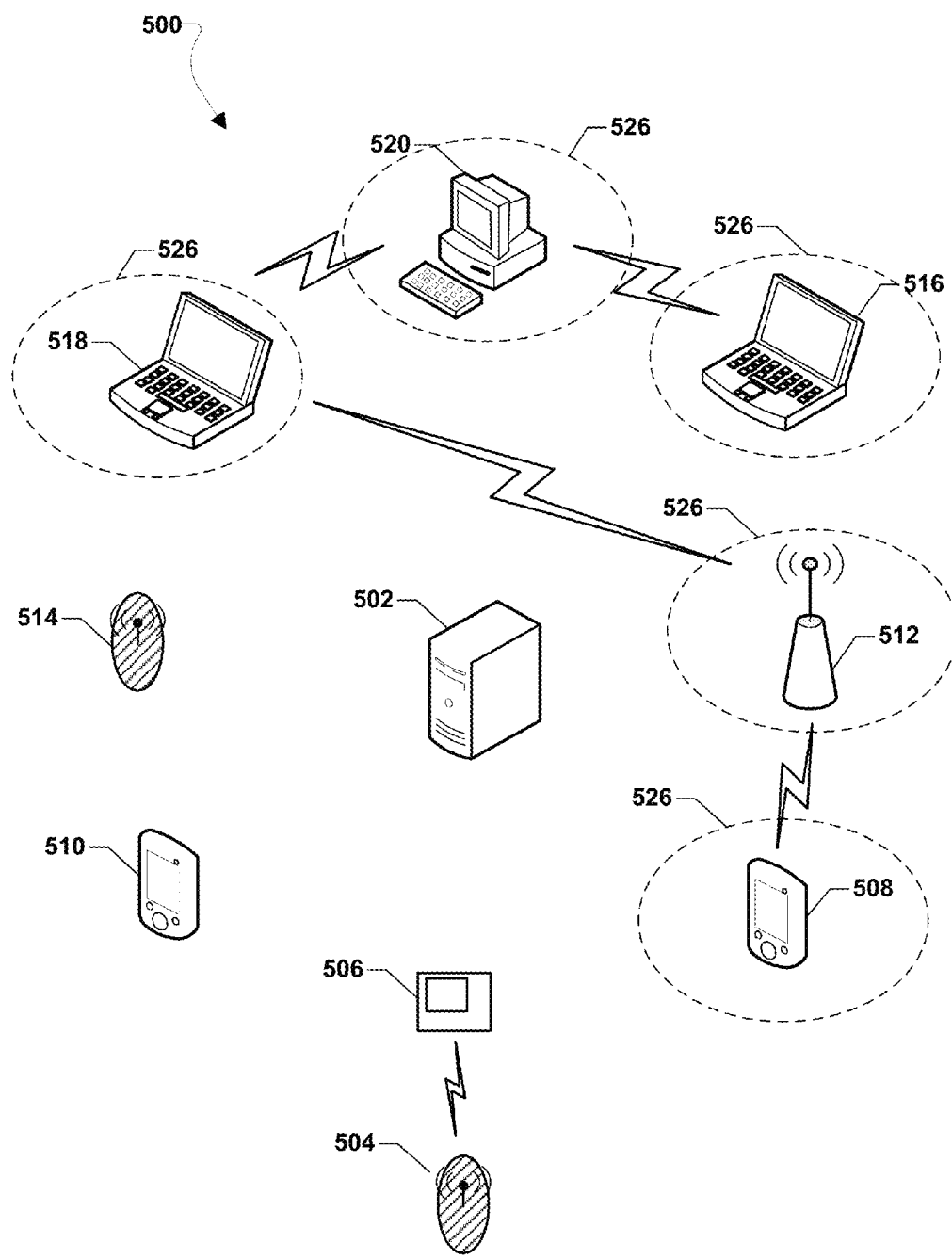

Based on the received communication characteristics 524, the server 502 may determine a list or set of qualified nodes 526 for use in transmitting the medical data as illustrated in FIG. 5D. The server 502 may determine a communications standard for transmitting the medical data, which may be a medical regulatory standard that is based on the priority or characteristics of the medical data being transmitted. The server 502 may compare the communications standards to the communication characteristics 524 of each node to determine which nodes are capable of transmitting the medical data in accordance with the communications standards. For example, in FIG. 5D the server 502 has identified the mobile device 508, the base station 512, and the computing devices 516, 518, and 520 as the qualified nodes 526. The medical sensor 514 and the mobile device 510 may not be qualified nodes for a variety of reasons, such as the nodes are not be capable of transmitting the medical data in accordance with the communications standard (e.g. too little bandwidth, slow transmission rate).

Figure 5E:
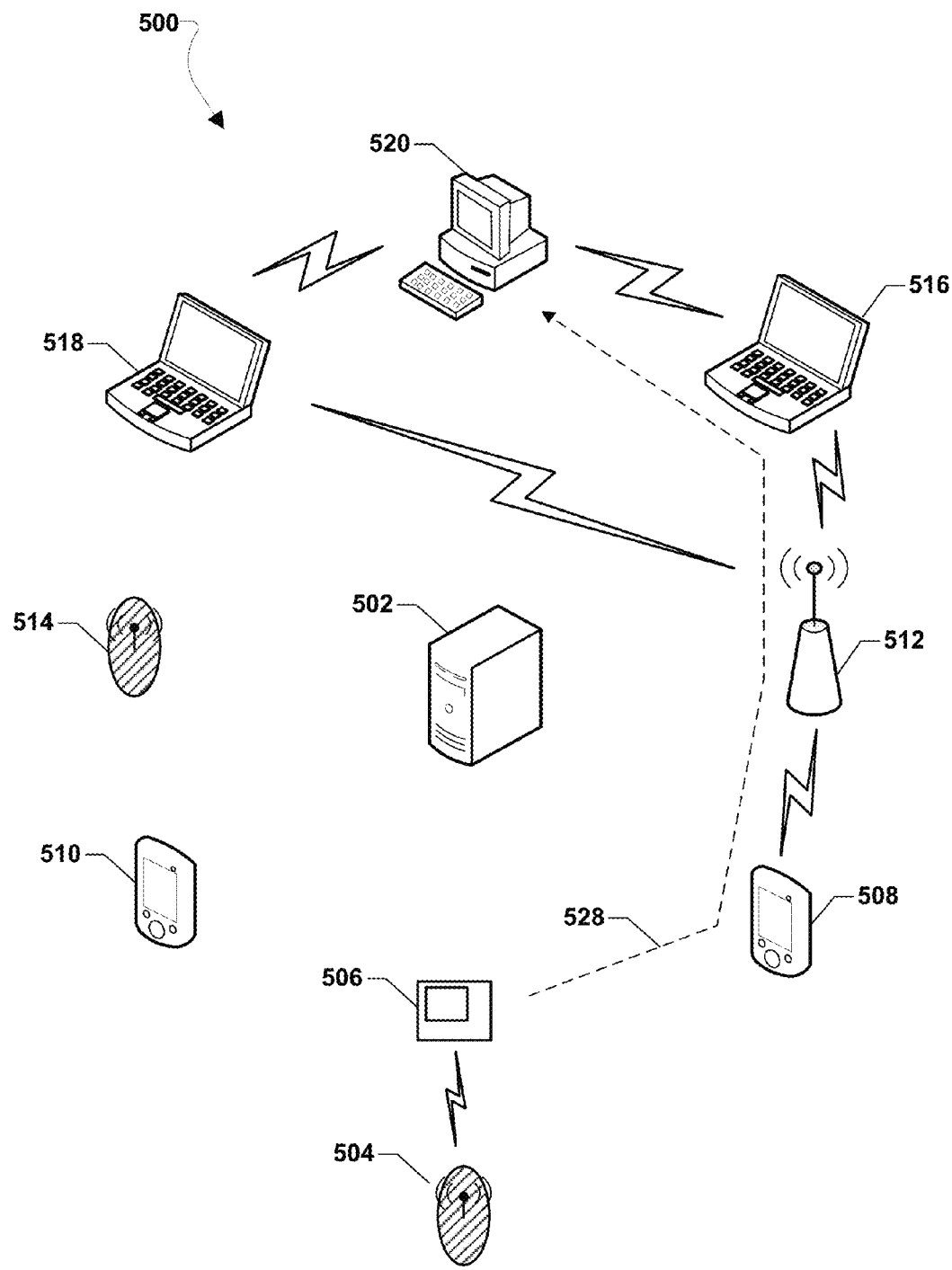

After determining the qualified nodes 526, the server 502 may determine a transmission path 528 from the medical analyzer 506 to the computing device 520 using one or more of the qualified nodes 526 as illustrated in FIG. 5E. The transmission path 528 goes from the medical analyzer 506 to the mobile device 508, to the base station 512, to the computing device 516, and finally to the destination computing device 520. FIG. 5E illustrates only one of several possible transmission paths and is not intended to be limiting in any way. The server may determine the transmission path 528 based on a number of factors, including but not limited to the total transmission distance, available bandwidth or other resources of each qualified node, the number of nodes used, and the characteristics of the medical data. For example, the server 502 may determine that the computing device 518 is already transmitting high priority medical data on another transmission path while computing device 516 is not transmitting any medical data, in which case the server 502 may include the computing device 516 in the transmission path instead of the computing device 518 even though the computing device 518 is a qualified node.

Figure 5F:
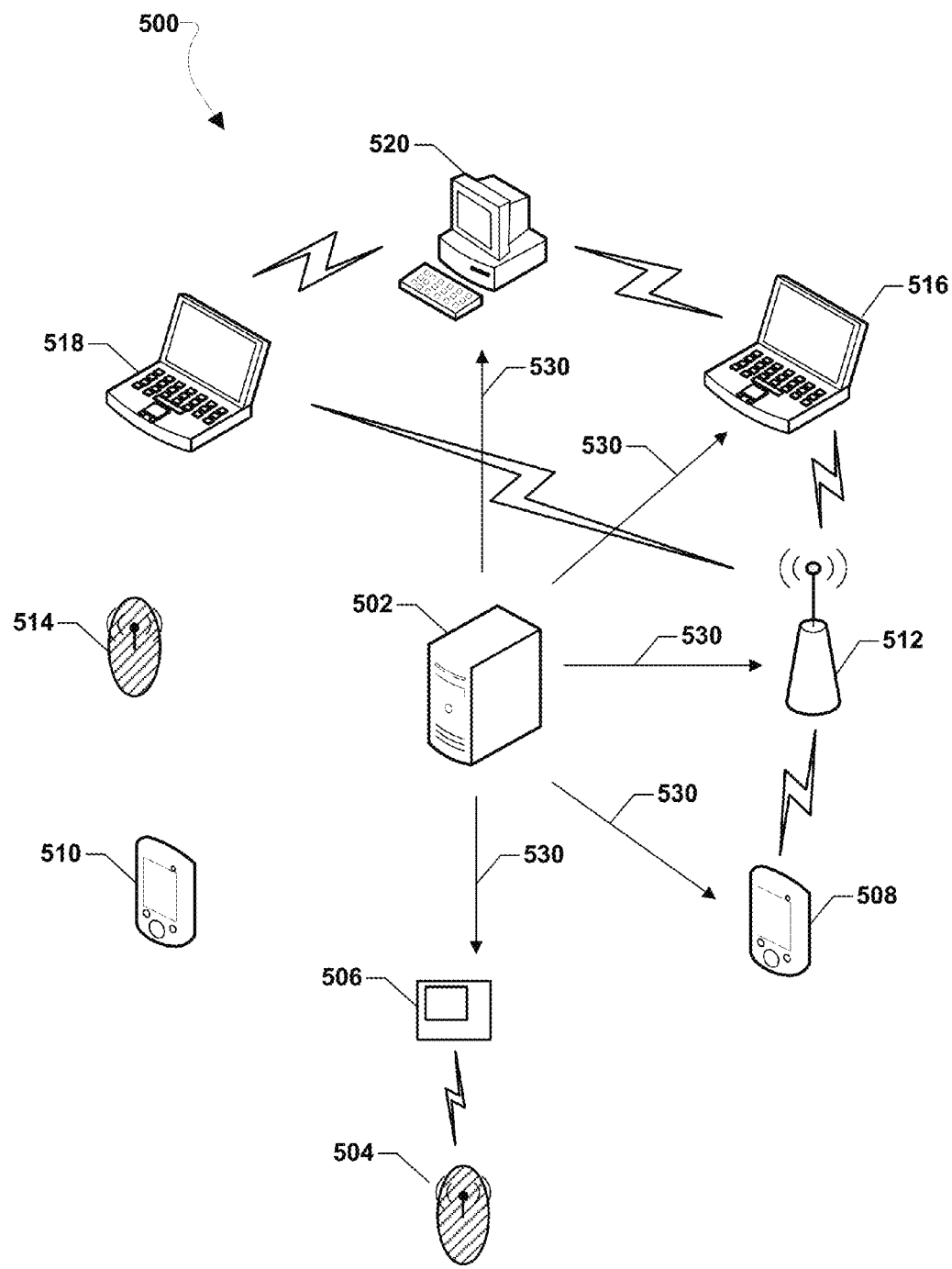

After determining the transmission path 528, the server may deputize each node in the transmission path by sending each node credentials 530 as illustrated in FIG. 5F. The credentials 530 may include one or more credentials 400 illustrated in FIG. 4. The credentials 530 may configure each node in the transmission path to communicate the medical data according to a communications standard, such as a medical regulatory standard. The credentials 530 may be stored in memory on each node and the credentials, or an application using the credentials, may act like a wrapper or abstraction layer between the processor of the node and various resources of the node.

Figure 5G:
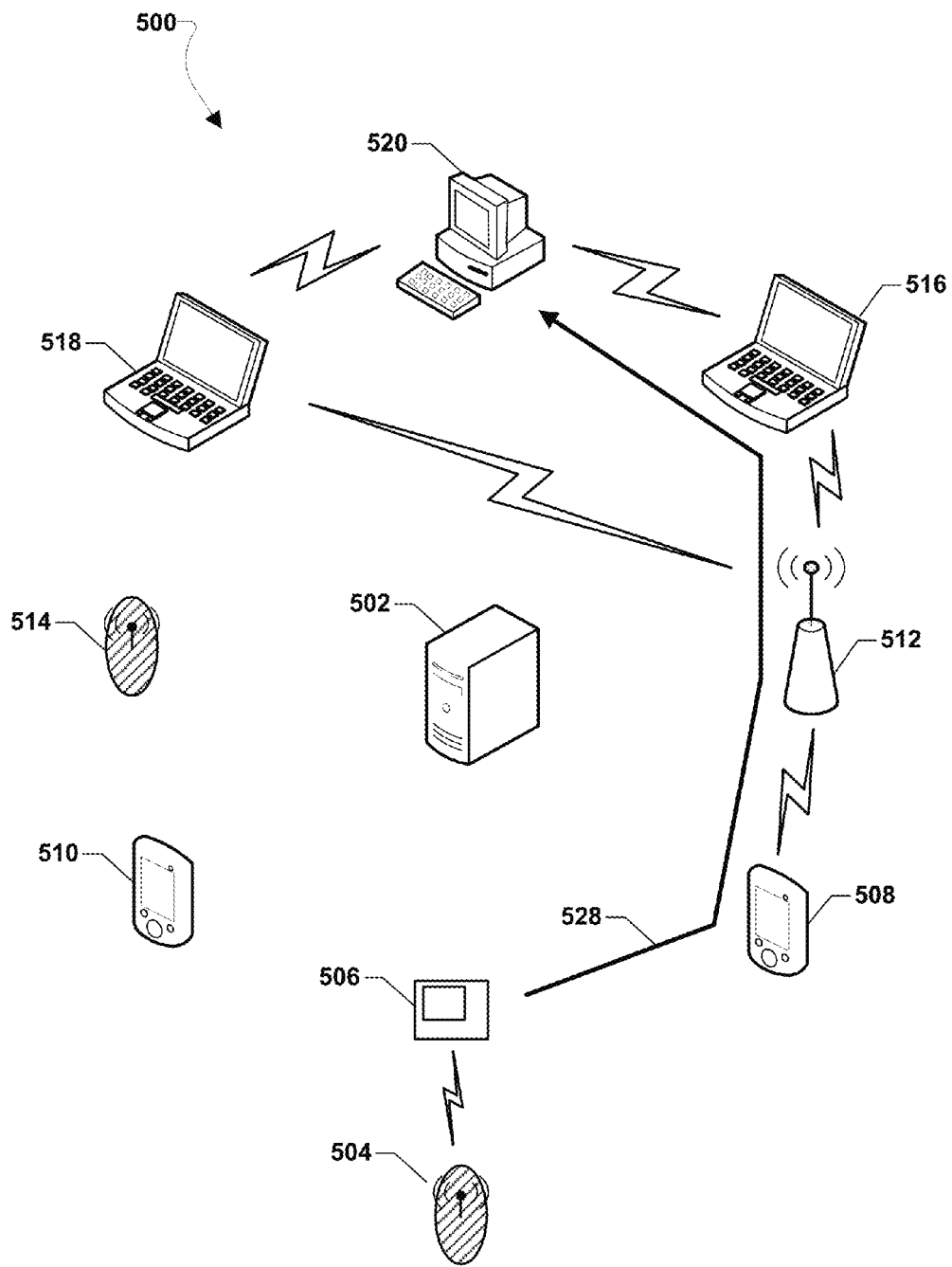

After the server 502 deputizes each node in the transmission path 528, the server 502 may instruct or allow the medical analyzer 506 to transmit the medical data through the transmission path 528 as illustrated in FIG. 5G. Each node in the transmission path 528 may use the stored credentials 530 to receive and transmit the data onwards in accordance with the communications standard appropriate for the specific medical data being transmitted. The server 502 may monitor the transmission of the medical data to ensure that the transmission is occurring in accordance with the appropriate communications standard. If the medical data is of high priority, the server 502 may establish multiple parallel transmission paths to ensure reliable transmission of the medical data.

Figure 5H:
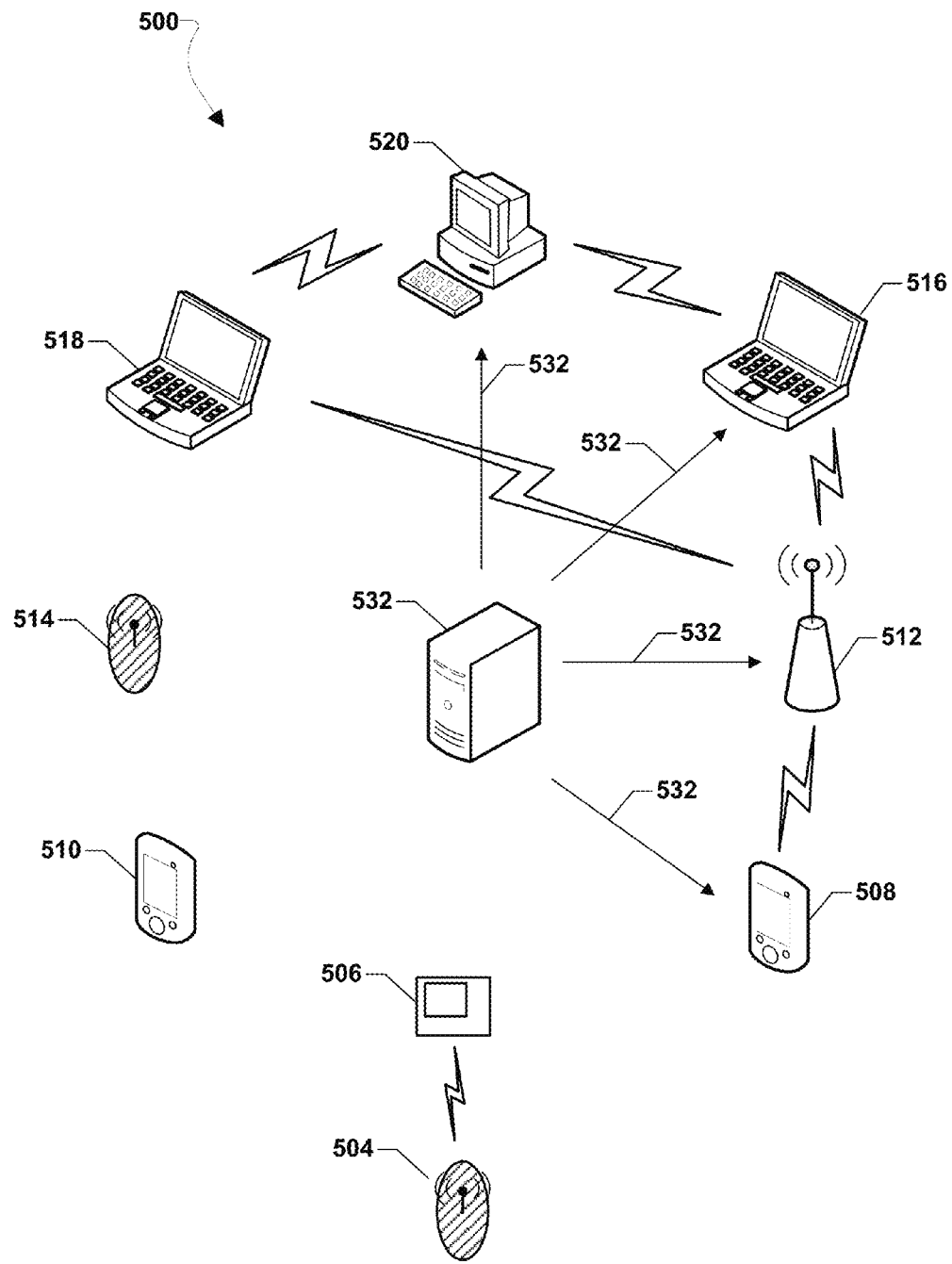

The transmission path 528 may persist until the medical analyzer 506 has finished transmitting the medical data. Once all the medical data has been transmitted, the server 502 may send messages 532 to each node in the transmission path 528 to disable or delete the credentials 530 as illustrated in FIG. 5H. Alternatively or in addition, each node may be configured to delete the credentials from memory after a period of no data communications or lack of network activity, thus ensuring that transmission paths will tear down automatically if communications with the server 502 are lost.

Each time medical data is transmitted through the medical data network 500, the server 502 and various nodes in the system may perform the operations illustrated in FIGS. 5A-5H for establishing a transmission path for the medical data. Once the transmission is finished, the server 502 unwinds the transmission path. In this manner, the server 502 is able to implement dynamic set-up and tear-down of transmission paths in the medical data network 500. By using the credentials 530, the server 502 also is capable of incorporating general computing devices into the transmission path even though such devices may not be specifically configured to transmit medical data in accordance with a communications standard.

The server 502 may also reroute the transmission path during communication of the medical data if the nature of the medical data changes (e.g., increasing in priority) or the topology of the medical data network 500 changes, such as if one or more nodes in the transmission path are removed or become unable to participate. FIGS. 6A-6G illustrate a medical data network 500 in which a server 502 dynamically reroutes the transmission path for medical data. Similar to FIGS. 5A-5H, the example medical data network 500 illustrated in FIG. 6A includes one or more servers 502 for controlling the transmission of medical data through the medical data network 500, a number of nodes in communication with server 502, such as medical sensors 504 and 514, a medical analyzer 506, mobile devices 508 and 510, a base station 512, and computing devices 516, 518, and 520. The medical data network 500 may include other nodes not illustrated in FIG. 6A. In the example illustrated in FIG. 6A, the medical sensor 504 is in communication with medical analyzer 506, the base station 512 is in communication with a mobile device 508 and a computing device 518, and the computing device 520 is in communication with computing devices 516 and 518. The mobile devices 508, 510, the base station 512, and the computing devices 516, 518, and 520 may be general computing devices in that the devices are not specifically configured to transmit medical data in accordance with a regulatory medical standard. Additionally, the medical devices 504, 506, and 514 may or may not be specifically configured to transmit medical data in accordance with a regulatory medical standard.

Figure 6A:
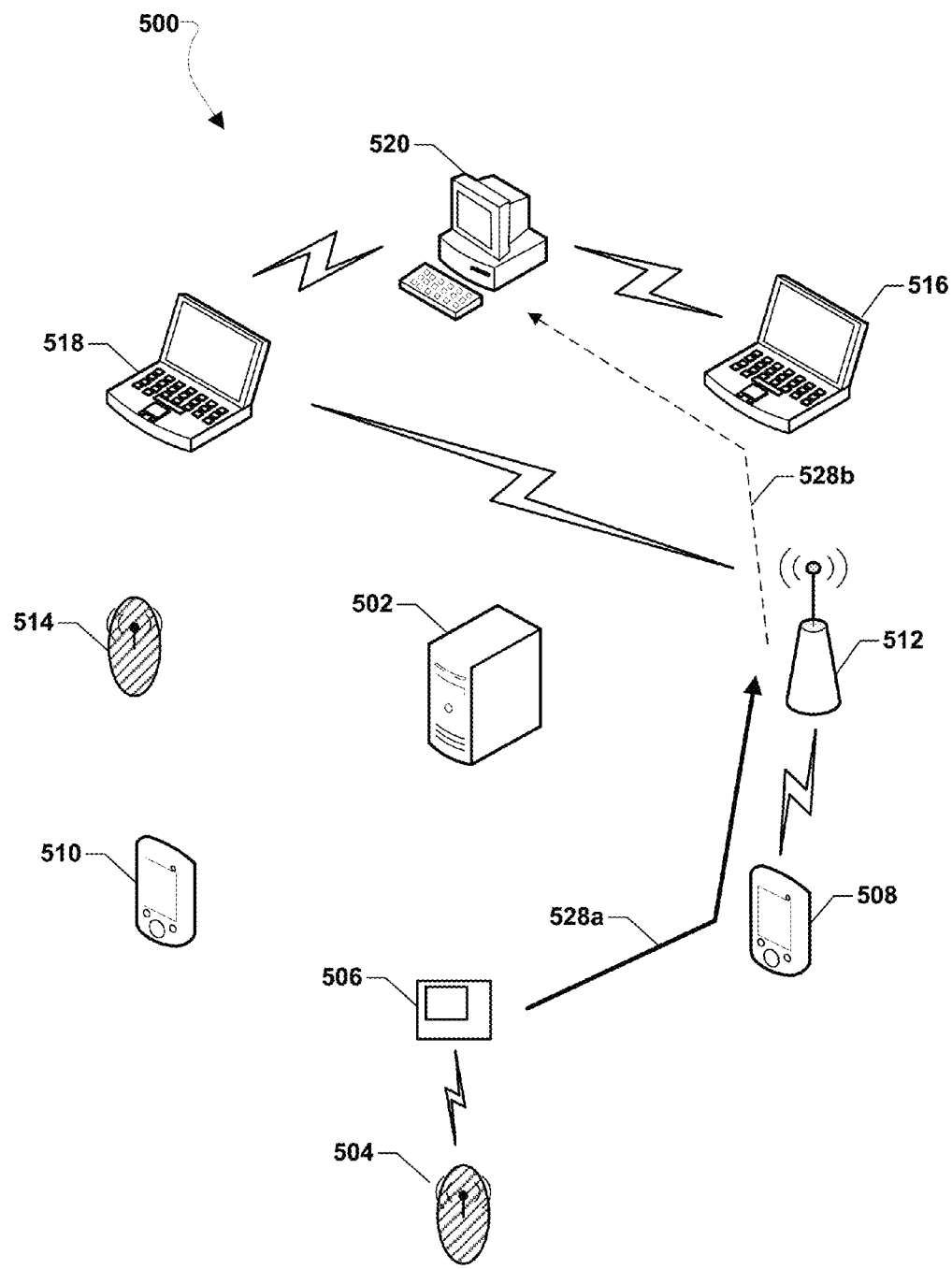
FIGS. 6A-6G illustrate a system for re-routing a transmission path in a medical data network in accordance with various embodiments.

In the example illustrated in FIG. 6A, the server 502 has set up a transmission path 528a and 528b between the medical analyzer 506 and the computing device 520, similar to the transmission path 528 illustrated in FIG. 5G. In the example illustrated in FIG. 6A, the base station 512 has lost the connection to the computing device 516 during transmission of the medical data. For example, the computing device 516 may have disconnected from the base station 512, left the coverage area of the base station 512, been shut off, or is busy transmitting other, higher priority medical data and thus does not have enough resources to continue supporting the transmission path 528. This means that the transmission path 528a stops at the base station 512 and cannot continue on to transmission path 528b to the computing device 520.

Figure 6B:
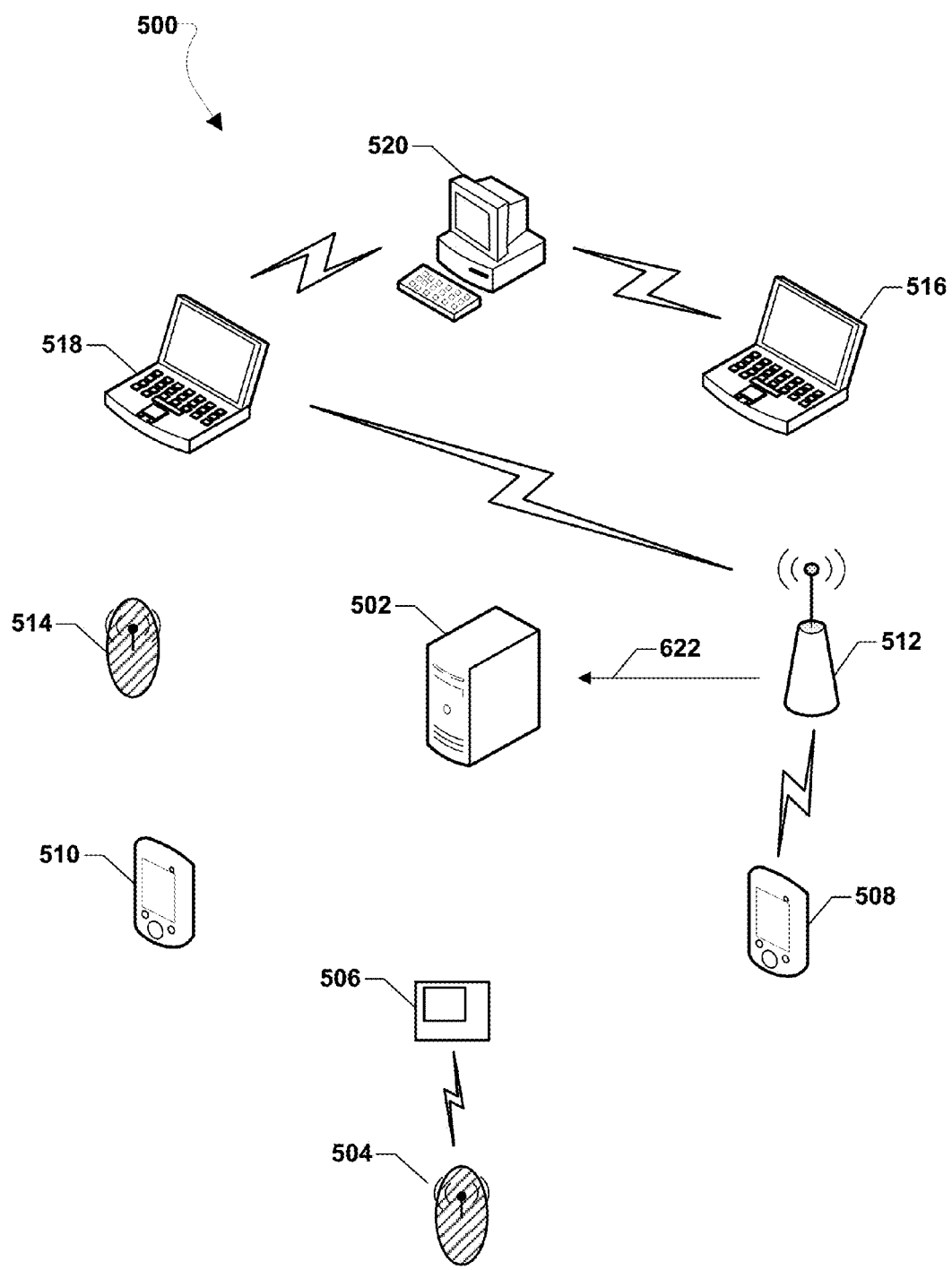
Figure 6C:
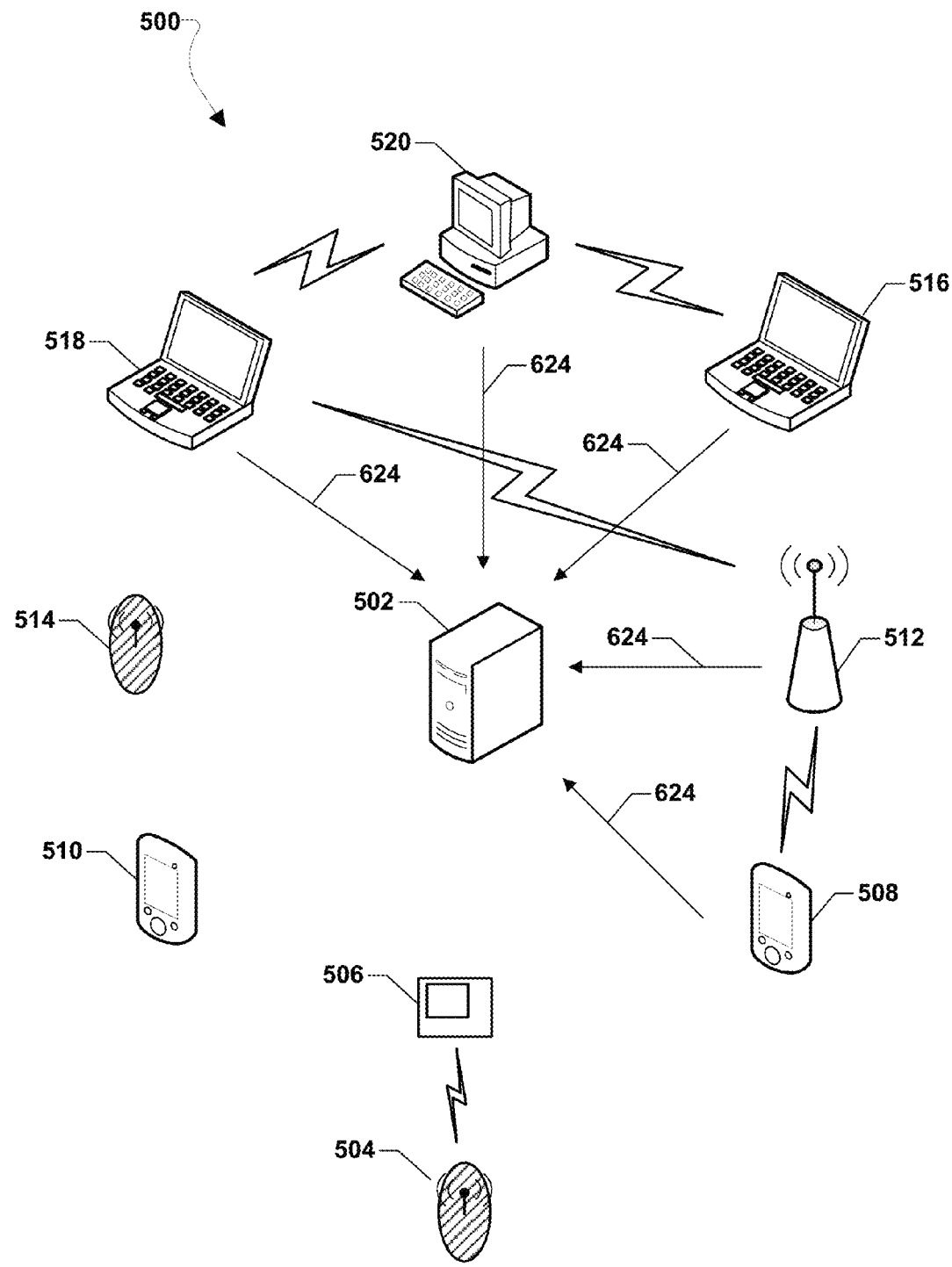

The base station 512 may detect that it can no longer communicate with the computing device 516, and in response may send a request 622 for an alternate transmission path to the server 502 as illustrated in FIG. 6B. In response to receiving the request 622, the server 502 may request and receive communication characteristics 624 from each node in the original set of qualified nodes as illustrated in FIG. 6C. The server 502 may also receive communication characteristics from other nodes in the medical data network 500 and may expand the set of qualified nodes as well, which is not illustrated in FIG. 6C. The server 502 may request each node to send the communication characteristics 624 to the server 502, or each node may independently send the communication characteristics 624 to the server 502 on a periodic or non-periodic basis.

Figure 6D:
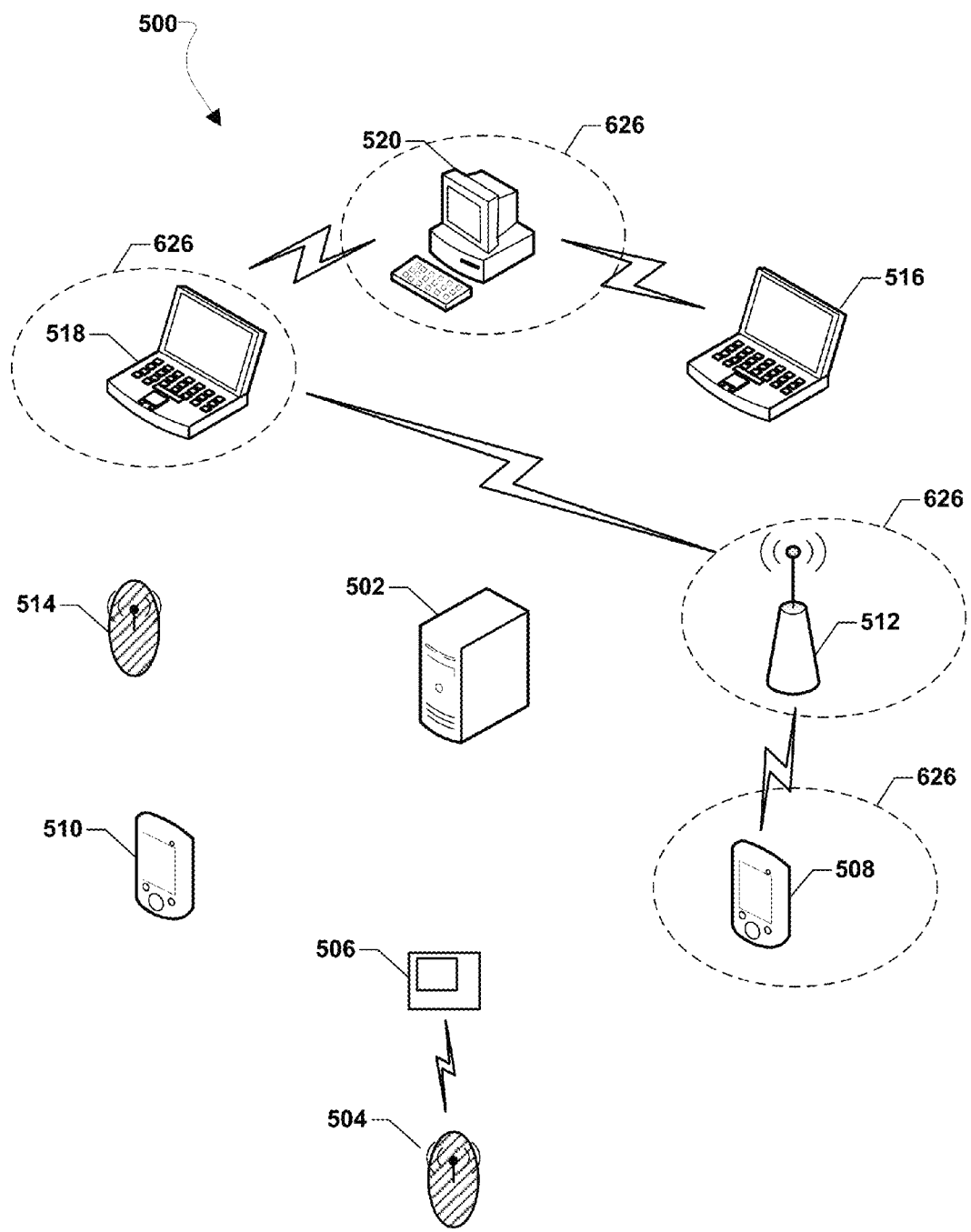

Based on the received communication characteristics 624, the server 502 may determine a new set of qualified nodes 626 to transmit the medical data as illustrated in FIG. 6D. The server 502 may determine a communications standard for transmitting the medical data, which may be a medical regulatory standard that is based on the priority or characteristics of the medical data. The server 502 may compare the communications standards to the communication characteristics 624 of each node to determine the nodes that are capable of transmitting the medical data in accordance with the communications standards. For example, in FIG. 6D the server 502 has identified the computing devices 518 and 520 as new qualified nodes 626 along with existing qualified nodes, the mobile device 508 and the base station 512. The computing device 516 is no longer a qualified node because it is not communicating with the base station 512.

Figure 6E:
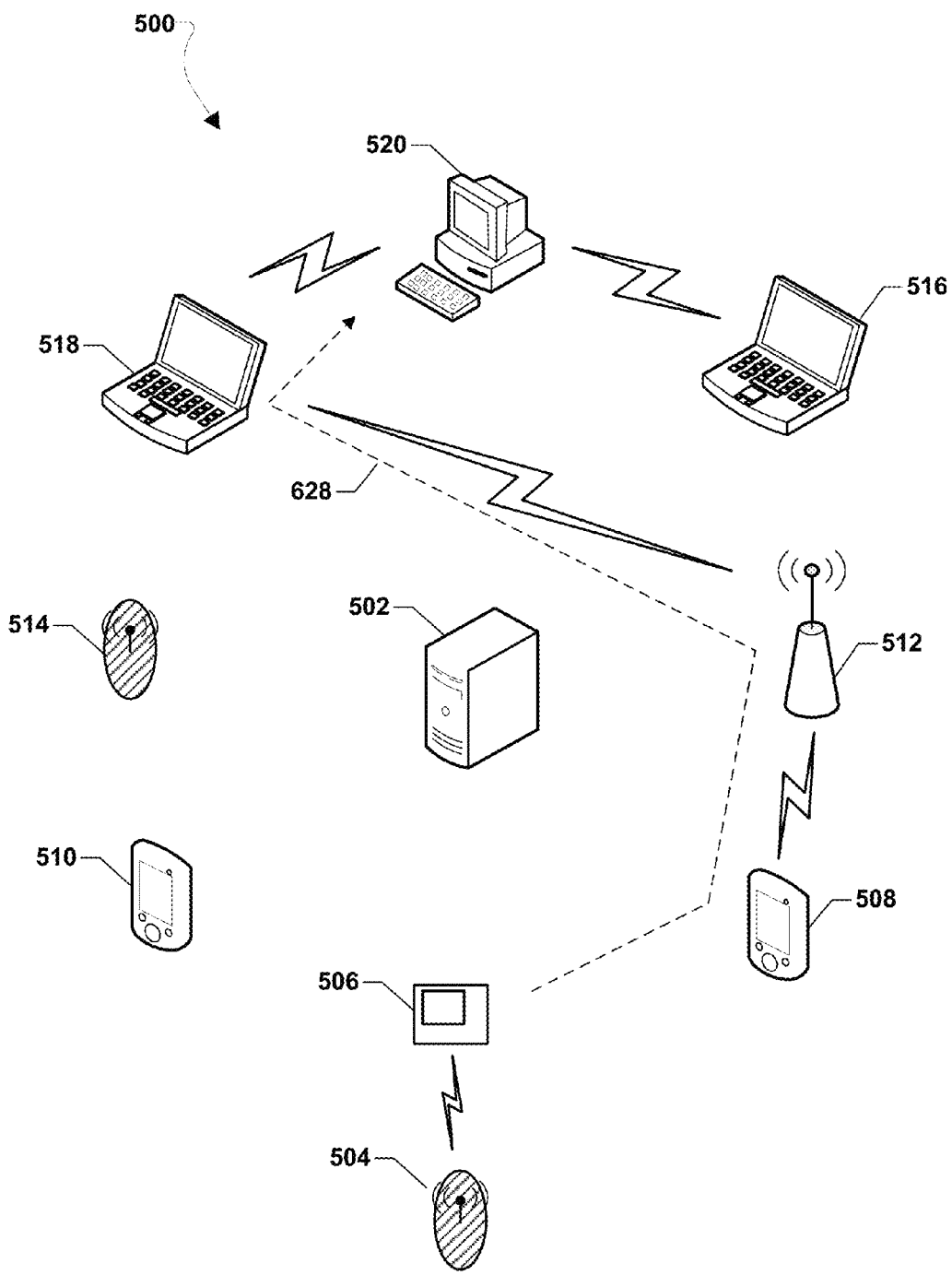

After determining the qualified nodes 626, the server 502 may determine an alternate transmission path 628 from the base station 512 to the computing device 520 using one or more of the qualified nodes 626 as illustrated in FIG. 6E. In the example illustrated in FIG. 6E, the alternate transmission path 628 goes from the medical analyzer 506 to the mobile device 508, to base station 512, to the computing device 518, to the destination computing device 520.

Figure 6F:
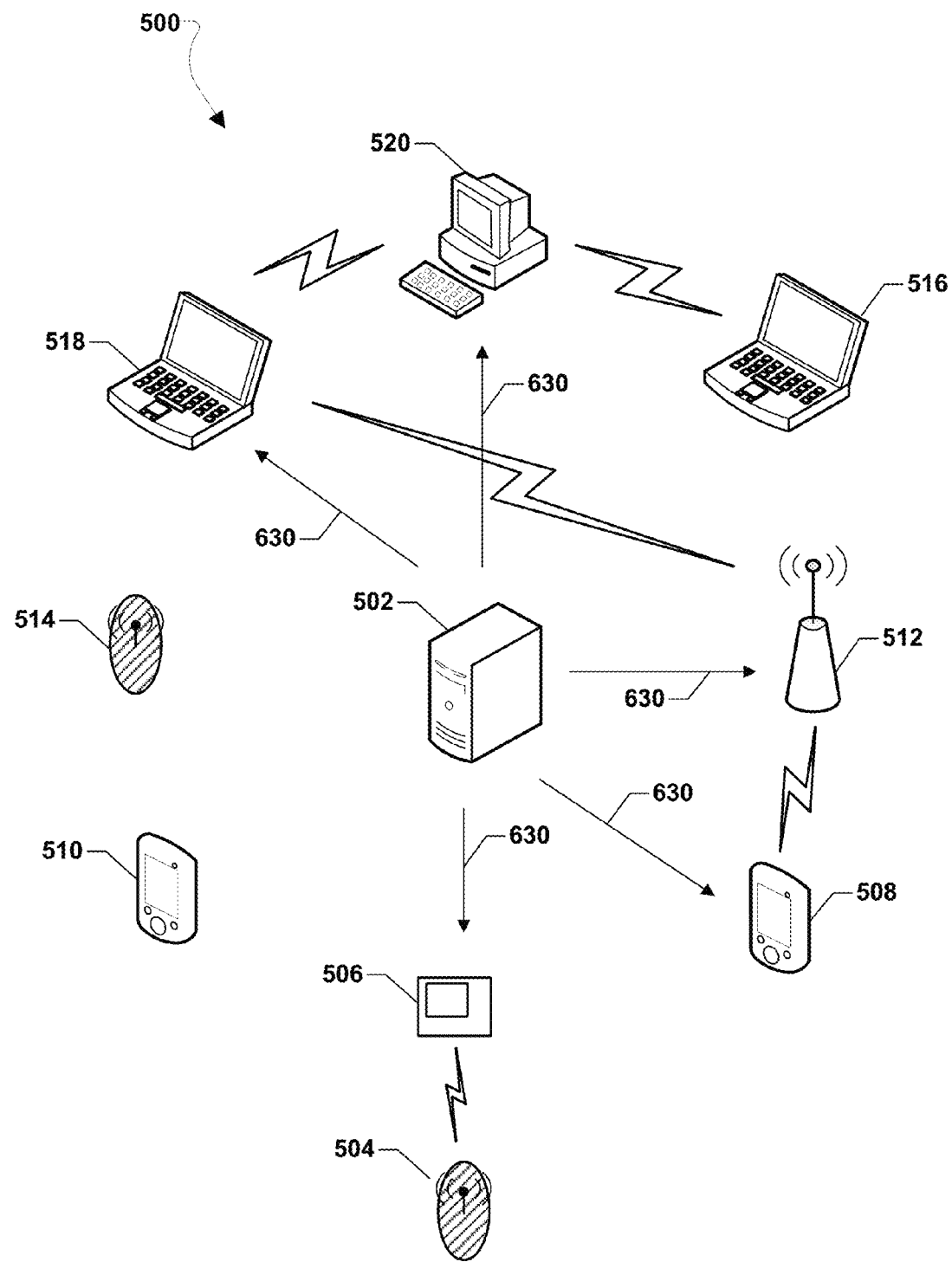

After determining the alternate transmission path 628, the server may deputize each node in the transmission path by sending each node credentials 630 as illustrated in FIG. 6F. The credentials 630 may include or more credentials 400 illustrated in FIG. 4. The credentials 630 may be different from the original credentials 530 sent to the nodes when the original transmission path 528 was first established. For example, the new credentials 630 may contain information about the alternate transmission path 628, such identifiers or addresses of the adjacent nodes in the transmission path. The credentials 630 may configure each node in the transmission path to communicate the medical data according to a communications standard, such as a medical regulatory standard. The credentials 630 may be stored in memory on each node, and the credentials, or an application using the credentials, may act like a wrapper or abstraction layer between the processor of the node and various resources of the node.

Figure 6G:
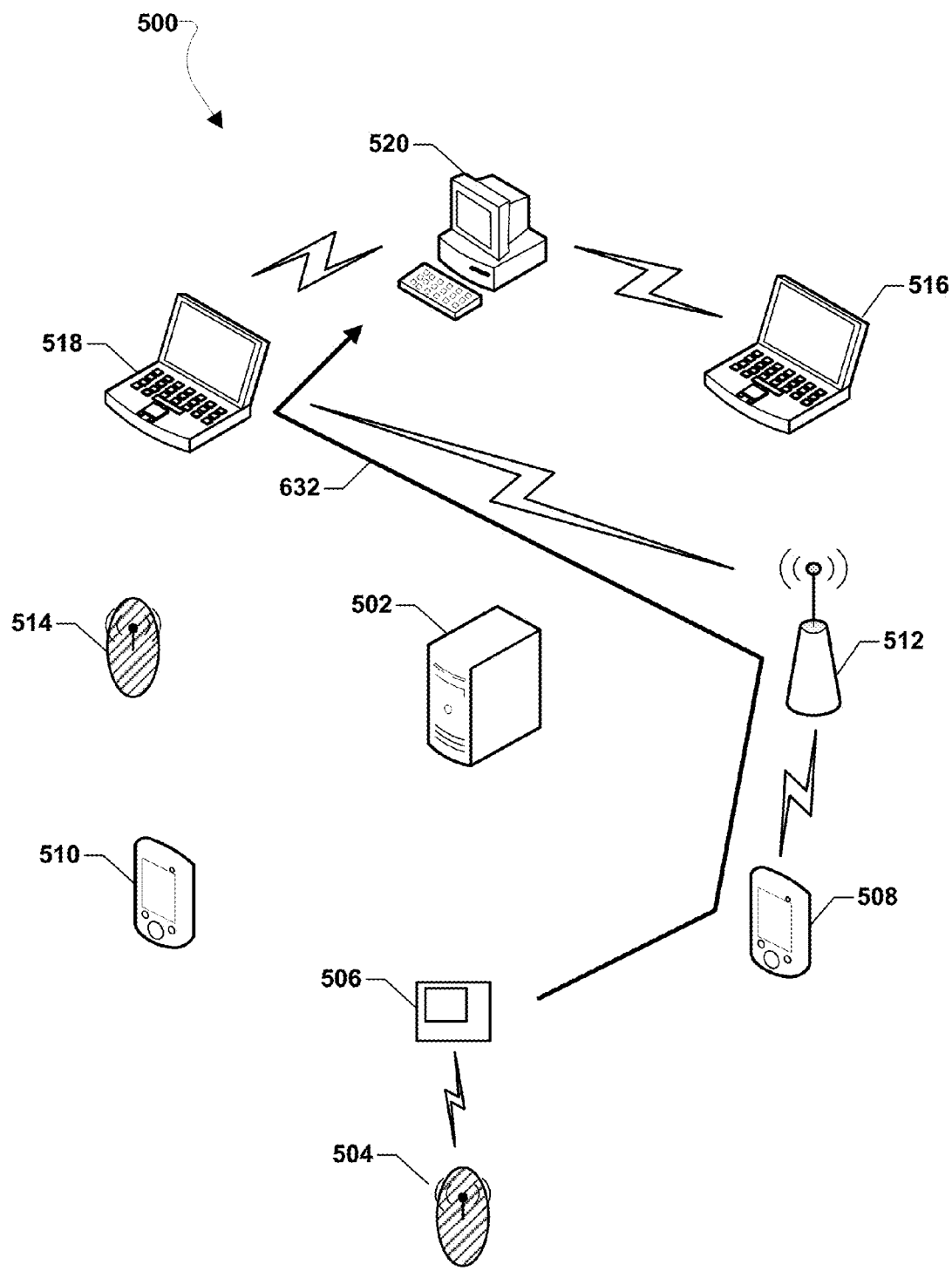

After the server 502 deputizes each node in the alternate transmission path 628, the server 502 may instruct the medical analyzer 506 and the base station 512 to transmit the medical data through the new transmission path 632 as illustrated in FIG. 6G. Each node in the new transmission path 632 uses the stored credentials 630 to receive and transmit the data onwards in accordance with the communications standard. The server 502 may monitor the transmission of the medical data to ensure that the transmission is occurring in accordance with the communications standard. In this manner, the server 502 is able to alter or reroute the transmission path of medical data due to changes in the medical data network 500.

Figure 7A:
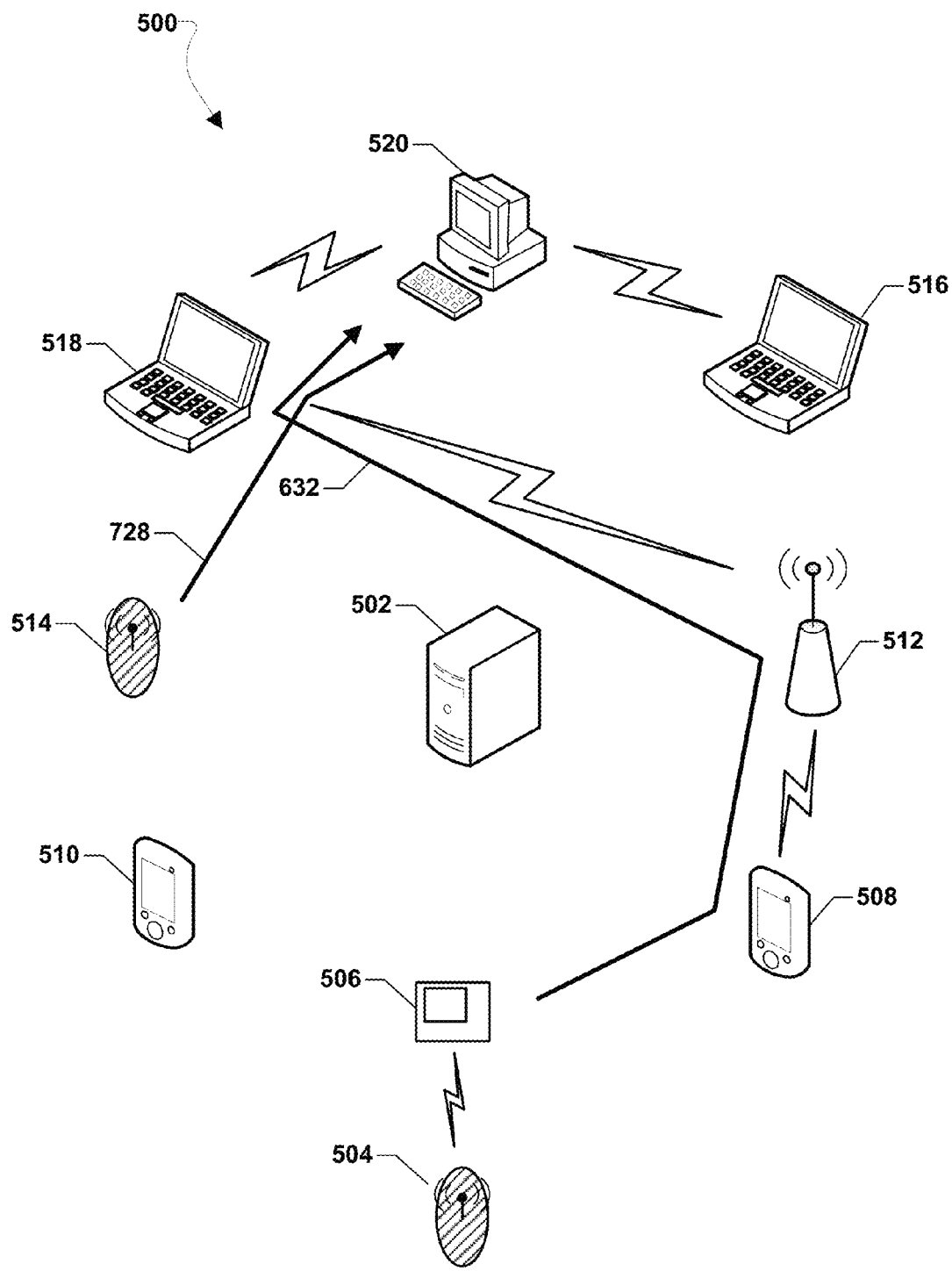
FIGS. 7A-7B illustrate a system for determining priority of transmission paths in a medical data network in accordance with various embodiments.
Figure 7B:
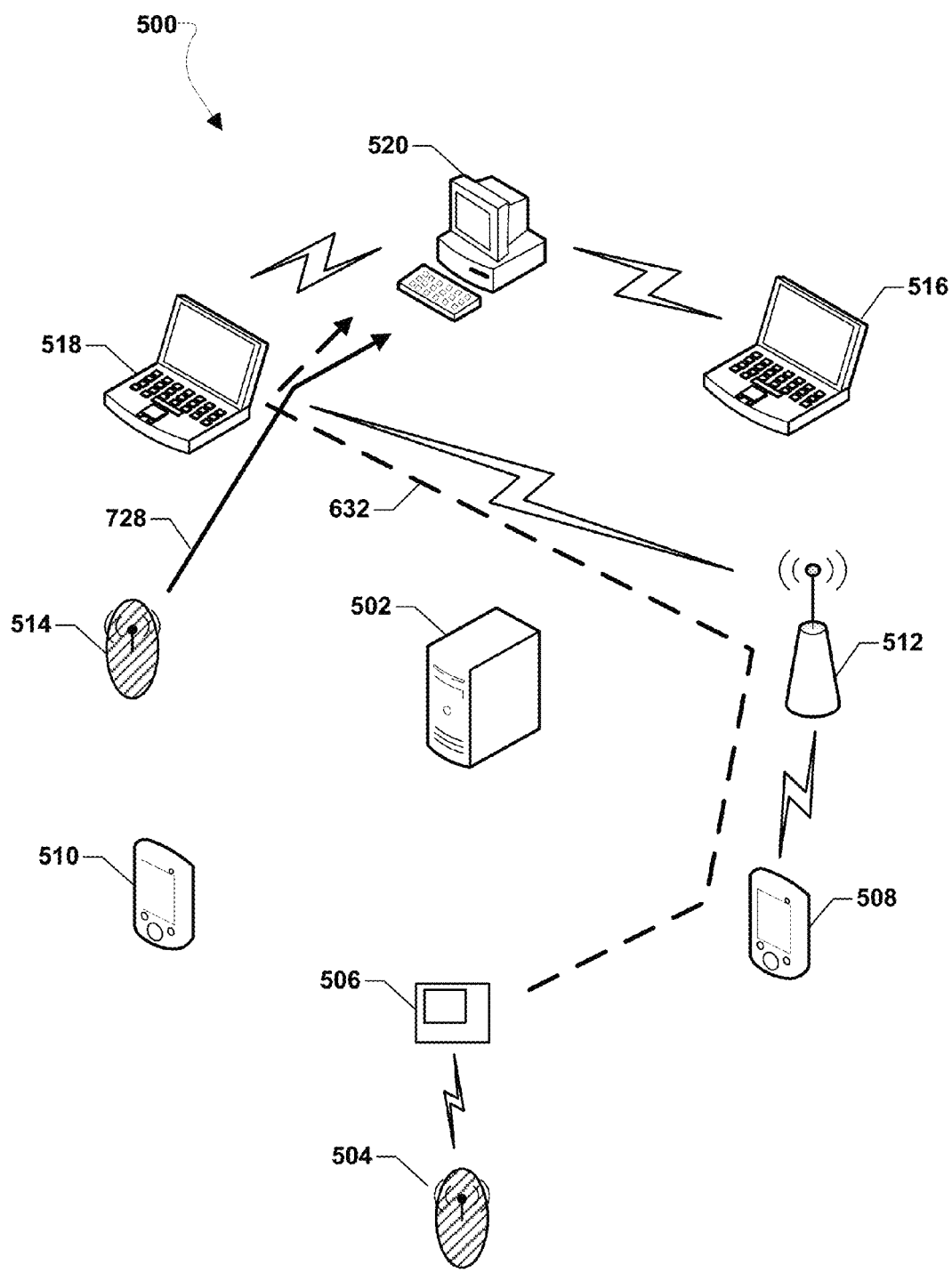

The server 502 may also manage multiple competing transmission paths in the medical data network 500. FIGS. 7A and 7B illustrate a medical data network 500 in which a server 502 may determine priorities among various transmission paths. Similar to the examples illustrated in FIGS. 5A-6G, the example medical data network 500 illustrated in FIG. 7A includes one or more servers 502 for controlling the transmission of medical data through the medical data network 500, a number of nodes in communication with server 502, such as medical sensors 504 and 514, medical analyzer 506, mobile devices 508 and 510, base station 512, and computing devices 516, 518, and 520. The medical data network 500 may include other nodes not illustrated in FIG. 6A. In the example illustrated in FIG. 7A, the medical sensor 504 is in communication with a medical analyzer 506, the base station 512 is in communication with a mobile device 508 and a computing device 518, and the computing device 520 may be in communication with computing devices 516 and 518. The mobile devices 508, 510, the base station 512, and the computing devices 516, 518, and 520 may be general computing devices in that the devices are not specifically configured to transmit medical data in accordance with a regulatory medical standard. Additionally, the medical devices 504, 506, and 514 may or may not be specifically configured to transmit medical data in accordance with a regulatory medical standard.

In the example illustrated in FIG. 7A, the server 502 has set up a transmission path 632 to transmit medical data from the medical analyzer 506 to the computing device 520. A medical sensor 514 may also request the server to set up another transmission path 728 so that the medical sensor 514 may transmit medical data to the computing device 520. The server may establish the transmission path 728 in a method similar to that described above with reference to FIGS. 6A-6G for the transmission path 632. In other words, the server 502 may receive communication characteristics from each node in the medical data network 500, identify qualified nodes to transmit the medical data, determine the transmission path 728 for the medical data, and deputize each node in the transmission path 728 with credentials that allow the nodes to transmit the medical data.

In the example illustrated in FIG. 7A, both of the transmission paths 632 and 728 include a common node in the computing device 518. The computing device 518 may also be supporting other transmission paths or may be conducting other operations as well. The computing device 518 may have a finite amount of resources (e.g. memory, CPU time, bandwidth) to handle communications, and thus may not be able to support every transmission path that the server 502 may attempt to establish through the computing device 518. FIG. 7A illustrates a circumstance in which the computing device 518 has enough resources to support both transmission paths 632 and 728. For example, both transmission paths 632 and 728 may be of low priority and the amount of medical data transmitted may also be low, so the computing device 518 can support both transmission paths 632 and 728.

In contrast, FIG. 7B illustrates a circumstance in which the computing device 518 does not have enough resources to support both transmission paths 632 and 728. For example, the medical sensor 514 may be transmitting medical data with a high priority or criticality, and there may be a large amount of medical data to transmit. The computing device 518 may notify the server 502 that the computing device 518 does not have enough resources to support both transmission paths 632 and 728. In response, the server 502 may determine that the transmission path 728 has a higher priority than the transmission path 632 and therefore the transmission path 728 should be maintained. The server 502 may then instruct the computing device 518 to maintain the transmission path 728 and drop the transmission path 632. The server 502 may suspend the transmission path 632 while the transmission path 728 is still active, or may determine an alternate transmission path from the medical analyzer 506 to the computing device 520 that does not include the computing device 518, as described with reference to FIGS. 6A-6G for re-routing transmission paths.

Figure 8:
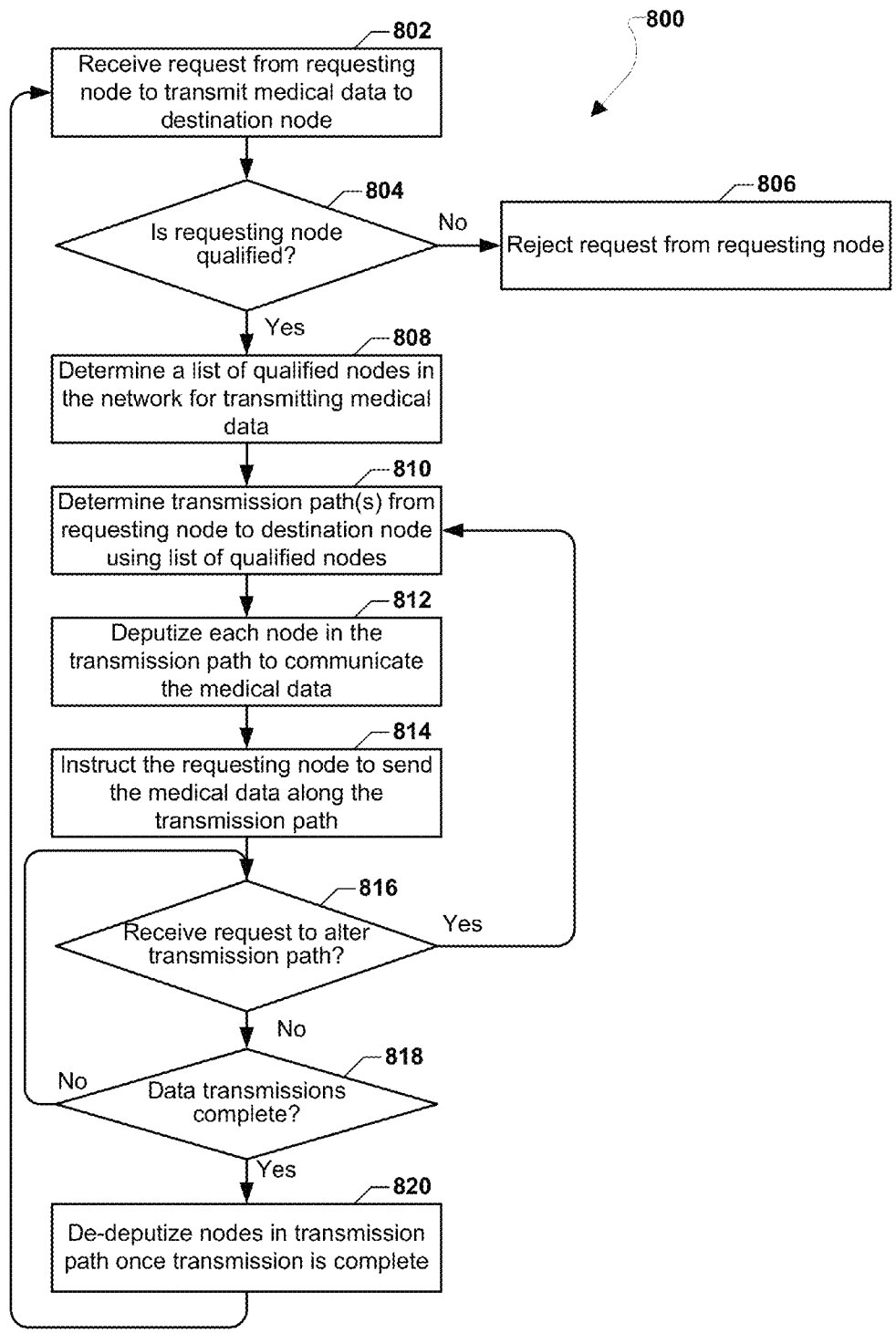
FIG. 8 is a process flow diagram illustrating a method for determining a transmission path for medical data in a network in accordance with various embodiments.

FIG. 8 illustrates an embodiment method 800 for determining a transmission path for medical data in a network. In an embodiment, the operations of method 800 may be performed by a server in a medical data network, such as the server 118 in FIG. 1, the server 280 in FIG. 2D, and the server 502 in FIGS. 5A-7B. Specifically, the operations of method 800 may be performed by a processor on a server executing processor-executable instructions stored on a non-transitory processor-readable medium (e.g., the general processor 282 executing processor-executable instructions stored in the memory 284 in FIG. 2D). The medical data network may be similar to the wireless network system 100 in FIG. 1 and the medical data network 500 in FIGS. 5A-7B.

In block 802, the server may receive a request from a requesting node to transmit medical data to a destination node. The requesting node or destination node may be a medical device, such as the wireless on-patient sensing device 200 in FIG. 2A or the medical analyzer 220 in FIG. 2B. The requesting node or destination node may also be general computing devices, such as base stations, tablets, desktop computers, laptops, smart phones, or other servers, such as a medical provider server. The medical data may include physiological data, a patient identifier, a regulatory classification, and a priority. The server may be in wireless or wired communication with the requesting node and other nodes in the medical data network.

In determination block 804, the server may verify whether the requesting node is qualified to participate in the medical data network and receive or transmit medical data. For example, the server may check a device identifier of the requesting node, and patient or provider identifiers provided by the requesting node. The server may compare the identifiers to a permissions database stored on the server or elsewhere (e.g., in a database accessible via another network) to determine whether the requesting node corresponds to a qualified device, patient, provider, or other parameter in the permissions database. In response to determining that the requesting node is not qualified to participate in the medical data network (i.e. determination block 804="No"), the server may reject or ignore the request from the requesting node in block 806.

In response to determining that the requesting node is qualified to participate in the medical data network (i.e. determination block 804="Yes"), the server may determine a list of qualified nodes in the network for transmitting the medical data from the requesting node to the destination node in block 808. The server may receive communication characteristics from a number of nodes in the medical data network and determine from the communication characteristics the nodes that are qualified nodes. An embodiment method for determining a list of qualified nodes is described in further detail with reference to FIG. 9.

In block 810, the server may determine at least one transmission path from the requesting node to the destination node using the list of qualified nodes. The transmission path(s) may be determined using a number of factors, including total transmission distance, available bandwidth or other resources of each node in the list of qualified nodes, the number of nodes used, and the priority of the medical data. For example, the server may establish a transmission path with the fewest nodes possible, or with nodes that provide the fastest transmission rate or largest bandwidth, or with nodes that are not currently supporting other transmission paths, or with nodes that are already configured to transmit data that is similar to the medical data from the requesting node (e.g. same priority, same destination node, same type of physiological data, same patient). The transmission path chosen may depend on characteristics of the medical data being transmitted, such as its priority.

In block 812, the server may "deputize" each node in the transmission path to communicate the medical data. Such deputizing operations may include sending each node in the transmission path credentials that configure the node to communicate the medical data in accordance with a communications standard. The communications standard may be a medical regulatory standard, such as those promulgated by the FDA or the European Commission Directorate General for Health and Consumers. The communications standard may depend on the characteristics of the medical data being transmitted, such as its priority. The credentials sent to the nodes in the transmission path may be similar to the credentials 400 illustrated in FIG. 4. For example, the credentials may include, but are not limited to, a patient identifier, a provider identifier, the identities of the requesting node, destination node, next node in the transmission path, and the previous node in the transmission path, a regulatory classification, a priority, a severity, a channel identifier, and a channel status. The credentials, or an application using the credentials, may act as a wrapper or abstraction layer on each node in order to format communication of the medical data to conform to the communications standard and to reserve the necessary resources of the node for transmission.

In block 814, the server may instruct the requesting node to begin communicating the medical data along the transmission path to the destination node. Each node in the transmission path communicates the medical data to the next node in accordance with the communications standard. The server may monitor the transmission to ensure that it is not interrupted and is transmitting in accordance with the communications standard, and may update the credentials of the nodes or otherwise instruct the nodes to support the transmission path if the medical data network conditions change. If the medical data being transmitted is of high priority, the server may establish multiple parallel transmission paths to ensure reliable transmission.

In determination block 816, the server may determine whether the server has received a request from an intermediate node in the transmission path to alter the transmission path. For example, the intermediate node may have determined that the medical data network topology has changed or that the next node in the transmission path is not functioning properly, and thus requests a reroute of the transmission path.

In response to determining that the server has received a request from an intermediate node in the transmission path to alter the transmission path (i.e. determination block 816="Yes"), the server may again determine an alternate transmission path from the intermediate node to the destination node in block 810, send updated credentials to each node in the alternate transmission path in block 812, and instruct the intermediate node to transmit the medical data through the alternate transmission path in block 814 (i.e. perform the operations in blocks 810, 812, and 814 with the intermediate node as the starting point). In some embodiments, the server may also re-determine the list of qualified nodes in block 808 in order to add or remove nodes from the original list (not illustrated in FIG. 8).

In response to determining that the server has not received a request from an intermediate node in the transmission path to alter the transmission path (i.e. determination block 816="No"), the server may monitor the transmission of the medical data to determine whether the transmission is complete in determination block 818. So long as data transmissions are continuing (i.e. determination block 818="No"), the server may continue to monitor for requests to alter the transmission path in determination block 816 and for termination of data communications in determination block 818.

In response to determining that data transmissions are complete (i.e. determination block 818="Yes"), the server may "de-deputize" each node in the transmission path, for example by instructing each node to delete or disable the credentials stored on the node. This effectively dismantles the transmission path for the medical data originating from the requesting node after the transmission is complete. A node may keep other credentials that are stored for other transmission paths that the node is currently supporting. The server may continue to monitor for requests to transmit medical data in block 802 and repeat the operations of the method 800 whenever there is a need to transmit medical data. In this manner, the method 800 provides for the dynamic routing of medical data through an ad hoc medical data network that may include the use of general computing devices that are not specifically configured to transmit medical data in accordance with a communications standard.

Figure 9:
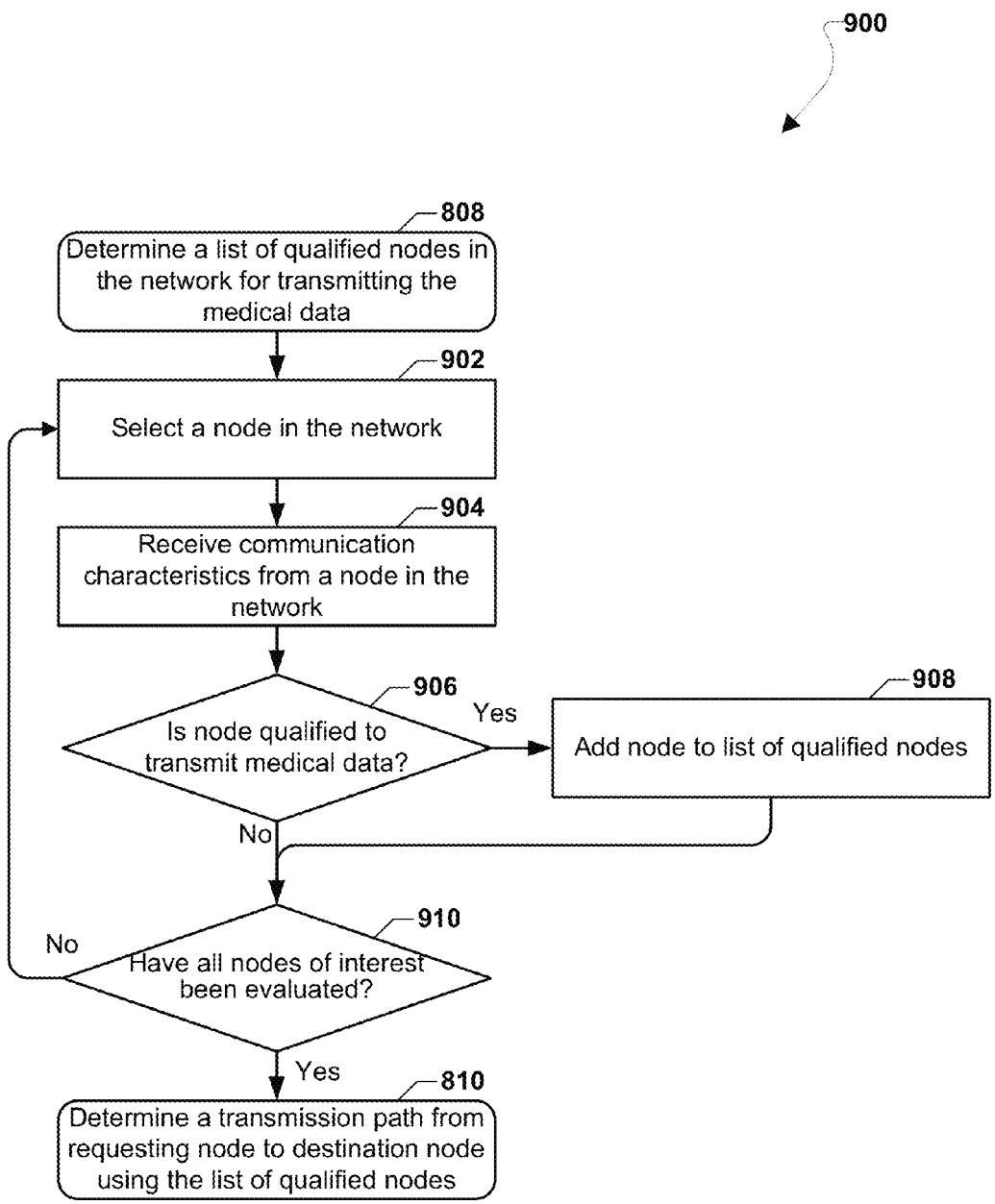
FIG. 9 is a process flow diagram illustrating a method for determining qualified nodes in a medical data network in accordance with various embodiments.

FIG. 9 illustrates an embodiment method 900 for determining a list of qualified nodes in a medical data network for transmitting medical data suitable for implement the operations of block 808 in the method 800 (FIG. 8). In an embodiment, the operations of method 900 may be performed by a server in a medical data network, such as the server 118 in FIG. 1, the server 280 in FIG. 2D, and the server 502 in FIGS. 5A-7B. Specifically, the operations of the method 900 may be performed by a processor on a server executing processor-executable instructions stored on a non-transitory processor-readable medium (e.g. the general processor 282 executing processor-executable instructions stored in the memory 284 in FIG. 2D). The medical data network may be similar to the wireless network system 100 in FIG. 1 and the medical data network 500 in FIGS. 5A-7B.

In block 902, the server may select a node in the medical data network for evaluation. The node may be selected from all the nodes in communication with the server, or may be selected from a certain subset of nodes (e.g. nodes that are near the requesting node or destination node, or nodes in certain other locations). The node may be a medical device, such as the wireless on-patient sensing device 200 in FIG. 2A or the medical analyzer 220 in FIG. 2B. The node may also be a general computing device, such as base stations, tablets, desktop computers, laptops, smart phones, or other servers, such as a medical provider server.

In block 904, the server may receive communication characteristics from the node. The server may request the node to send the communication characteristics, or the node may independently send the communication characteristics to the server on a periodic or non-periodic basis. The communication characteristics may include any of the communication characteristics 300 illustrated in FIG. 3. For example, the communication characteristics may include, but are not limited to, device type or identifier, MAC address, a communications range, data transmission rate, data reception rate, regulatory classification, collected medical data, event triggers, interface requirements, bandwidth capability, packet redundancy level, quality of service level, latency level, security capabilities, link redundancy level, and power level.

In determination block 906, the server may determine whether the node is qualified to transmit the medical data based on the communication characteristics of the node. The server may determine a communications standard for transmitting the medical data, which may be a medical regulatory standard that is based on the priority or characteristics of the medical data. The server may compare the communications standards to the communication characteristics the node to determine whether the node is capable of transmitting the medical data in accordance with the communications standards. For example, the communications standard may require a certain minimum transmission rate and the server may determine whether the node is capable of meeting the minimum transmission rate.

In response to determining that the node is qualified to transmit the medical data (i.e. determination block 906="Yes"), the server may add the node to a list or set of qualified nodes in block 908.

In response to determining that the node is not qualified to transmit the medical data (i.e. determination block 906="No"), or after adding a qualified node to the list of qualified nodes, the server may determine whether all nodes of interest have been evaluated in determination block 910. In some embodiments, the server may only evaluate a subset of nodes (e.g. nodes within a certain geographic area), or may evaluate all the nodes in the medical data network. In response to determining that all nodes of interest have not been evaluated (i.e. determination block 910="No"), the server selects another node in the network for evaluation, repeating the operations in blocks 902, 904, 906, and 908 for the new selected node.

In response to determining that all nodes of interest have been evaluated (i.e. determination block 910="Yes"), the server may determine a transmission path from the requesting node to the destination node using the list of qualified nodes in block 810 of the method 800 (FIG. 8). In this manner, the method 900 allows a server to evaluate nodes in a medical data network to determine whether they are suited to transmit medical data from a requesting node.

Figure 10:
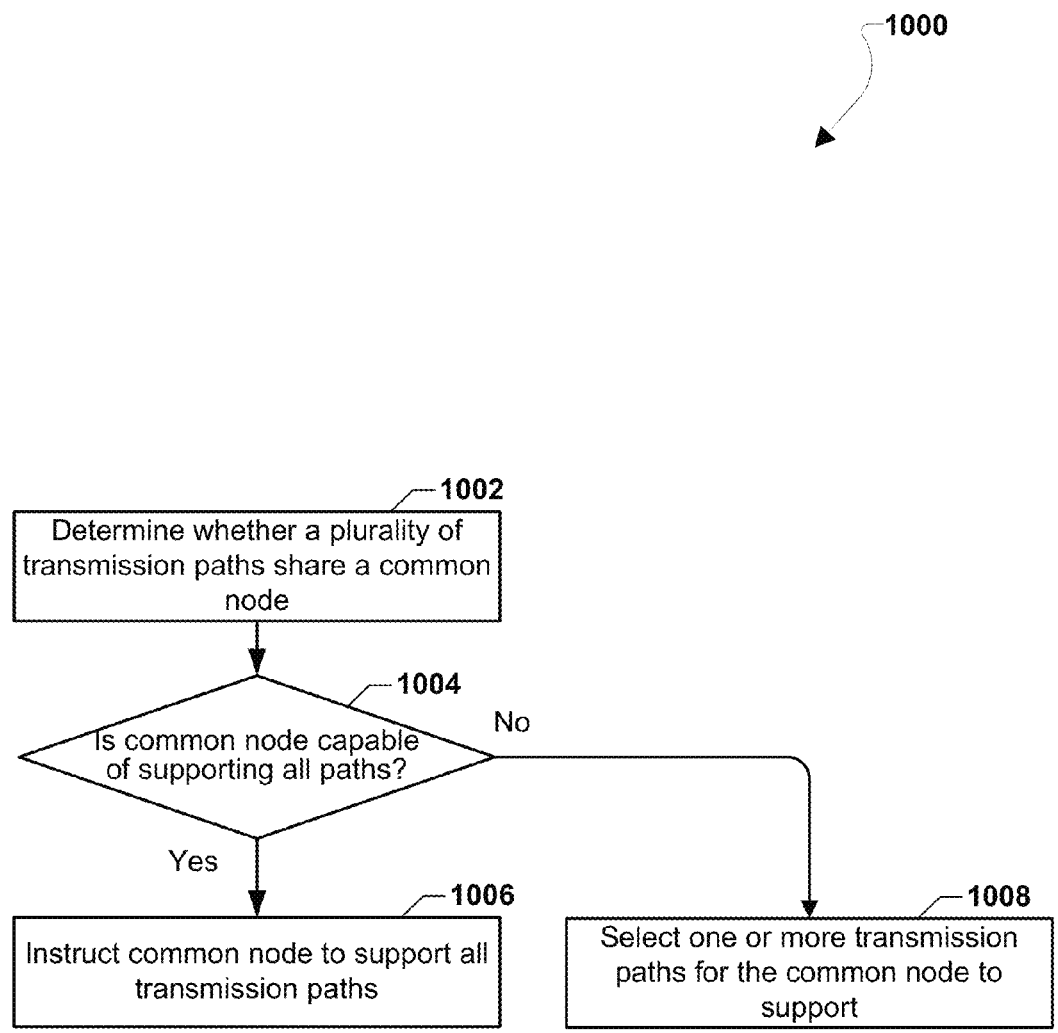
FIG. 10 is a process flow diagram illustrating a method for determining priority among transmission paths sharing a common node in accordance with various embodiments.

FIG. 10 illustrates an embodiment method 1000 for determining priority between transmission paths sharing a common node in a medical data network. In an embodiment, the operations of method 1000 may be performed by a server in a medical data network, such as the server 118 in FIG. 1, the server 280 in FIG. 2D, and the server 502 in FIGS. 5A-7B. Specifically, the operations of the method 1000 may be performed by a processor on a server executing processor-executable instructions stored on a non-transitory processor-readable medium (e.g. the general processor 282 executing processor-executable instructions stored in the memory 284 in FIG. 2D). The medical data network may be similar to the wireless network system 100 in FIG. 1 and the medical data network 500 in FIGS. 5A-7B.

In block 1002, the server may determine whether a plurality of transmission paths active in the medical data network share a common node. The common node may be a medical device or a general computing device, such as a base station, tablet, desktop computer, laptop, smart phone, or another server, such as a medical provider server. The common node may already be supporting one or more transmission paths for medical data, and the server has identified the common node as a node in a new transmission path for the transmission of new medical data.

In determination block 1004, the server may determine whether the common node is capable of supporting all of the transmission paths that run though the node. The server may receive information from the common node about the current or maximal resource capabilities of the common node, including bandwidth, memory, CPU time, and other factors. The server may also receive other information about the communication characteristics of the common node, such as the communication characteristics 300 in FIG. 3. Using this information, the server may determine whether the common node has enough resources to support all the transmission paths without violating the communications standards associated with each transmission path. For example, if the total minimum transmission rate of the transmission paths is 100 Mbps, and the common node is only capable of transmitting a maximum of 50 Mbps, the server may determine that the common node does not have enough resources to support all the transmission paths.

In response to determining that the common node is capable of supporting all the transmission paths (i.e. determination block 1004="Yes"), the server may instruct the common node to support all of the transmission paths in block 1006.

In response to determining that the common node is not capable of supporting all the transmission paths (i.e. determination block 1004="No"), the server may select one or more transmission paths for the common node to support in block 1008. The server may select among the various transmission paths according to the priority of the medical data on each path (e.g. support transmission of high priority medical data), the resource limitation of the common node, the availability of alternate routes for transmission paths, and other factors. The server may also suspend or reroute transmission paths that the server determines should not be supported by the common node. The server may then establish a different transmission path bypassing the common node for those data transmission not selected in block 1008, such as by performing operations of the methods 500 or 600 described above with reference to FIGS. 5 and 6. In this manner, the method 1000 allows a server in a medical data network to prioritize transmission paths utilizing common nodes, and to adjust various transmission paths based on current resource consumption of the nodes in the medical data network.

Figure 11:
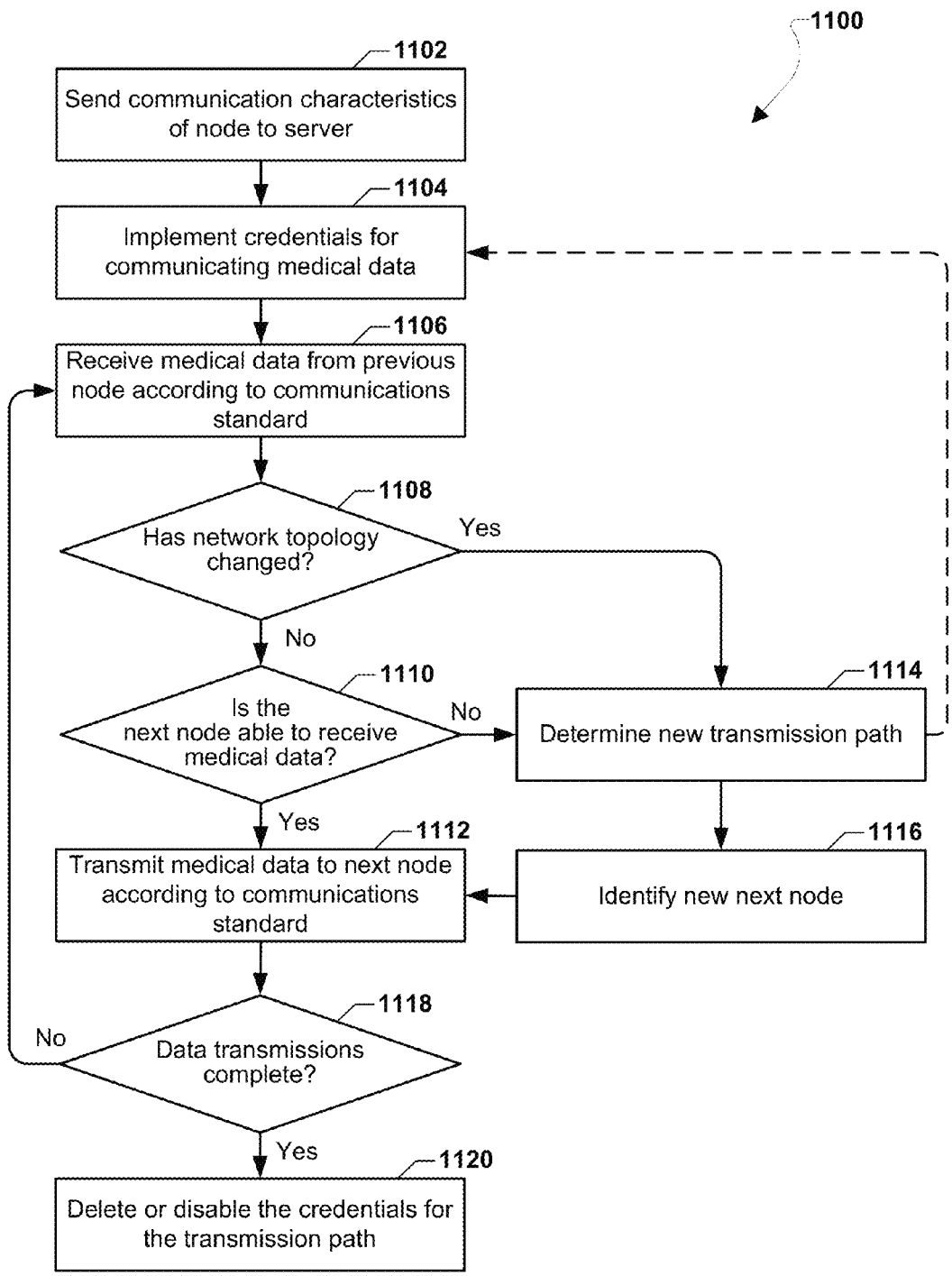
FIG. 11 is a process flow diagram illustrating a method for transmitting medical data in a network in accordance with various embodiments.
Figure 12:
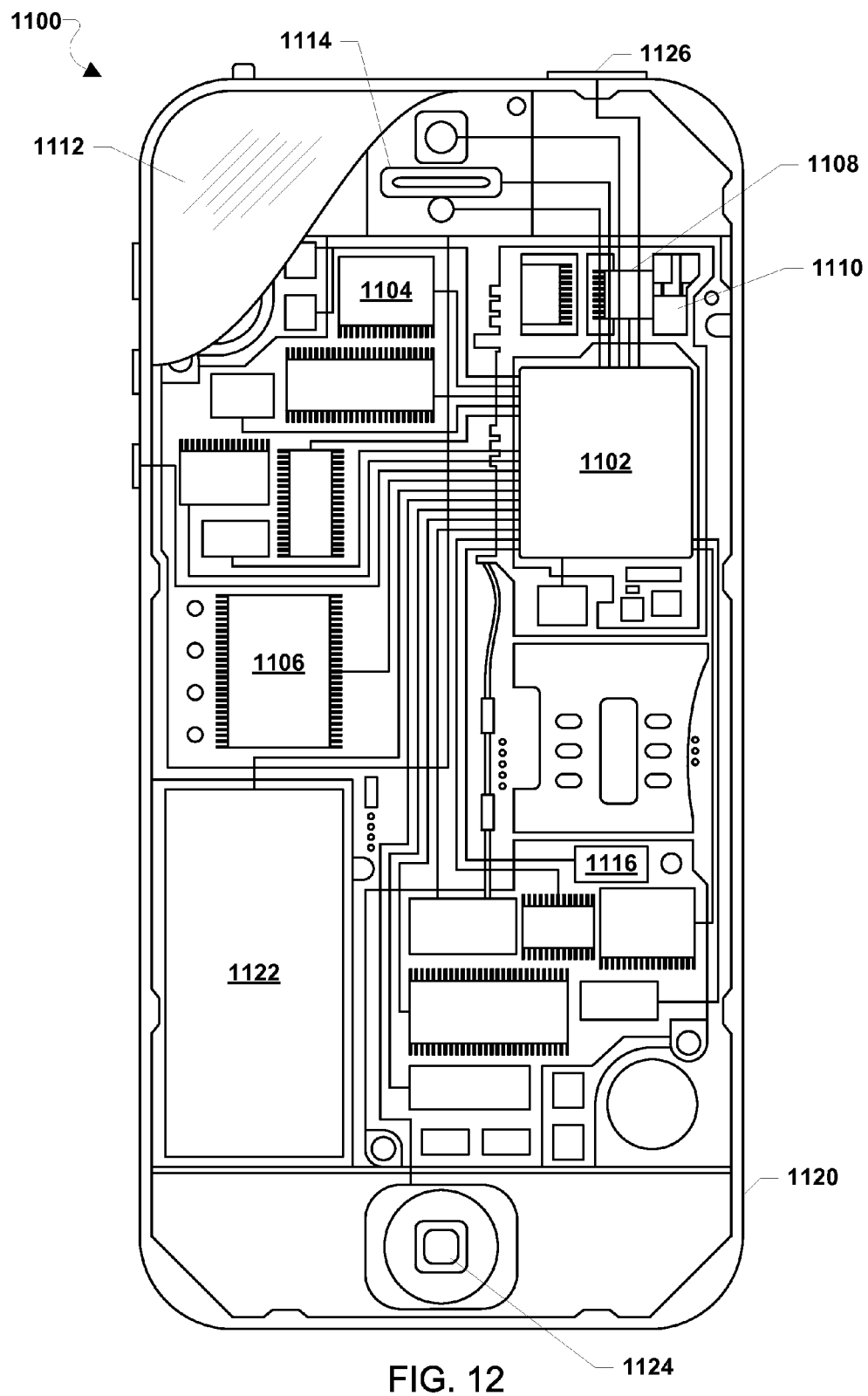
FIG. 12 is a component diagram of an example mobile device suitable for use with the various embodiments.

FIG. 11 illustrates an embodiment method 1100 for transmitting medical data in a medical data network. In an embodiment, the operations of method 1100 may be performed by a node in a medical data network. The node may be a medical device, such as the devices 104, 106, 200, and 220 in FIGS. 1-2B. The node may also be a general computing device, such as the base stations 110, 112 in FIG. 1, tablet, desktop computer, laptop, the smart phone 108 or 250 in FIGS. 1 and 2C, or another server, such as a medical provider server. Specifically, the operations of method 1100 may be performed by a processor of a node executing processor-executable instructions stored on a non-transitory processor-readable medium (e.g. the general processors 206, 222, 252 and the memory 208, 224, 254 with reference to FIGS. 2A-2C). The medical data network may be similar to the wireless network system 100 in FIG. 1 and the medical data network 500 in FIGS. 5A-7B.

In block 1102, the node may send communication characteristics of the node to a server controlling the medical data network. The node may send the communication characteristics in response to a request from the server, or may independently send the communication characteristics to the server on a periodic or non-periodic basis. The communication characteristics may include any of the communication characteristics 300 illustrated in FIG. 3. For example, the communication characteristics may include, but are not limited to, device type or MAC address, a communications range, data transmission rate, data reception rate, regulatory classification, collected medical data, event triggers, interface requirements, bandwidth capability, packet redundancy level, quality of service level, latency level, security capabilities, link redundancy level, and power level. In alternative embodiments, the node may initiate a transmission of medical data independently, without having to contact a server. In such alternative embodiments, communication characteristics of the node may already be available or previously stored at the server.

In block 1104, the node may implement credentials for communicating medical data through a transmission path according to a communications standard. The credentials may be received from the server, or may be previously stored in the node, or generated by the node. The communications standard may be a medical regulatory standard, such as those promulgated by the FDA or the European Commission Directorate General for Health and Consumers. The communications standard may depend on the characteristics of the medical data being transmitted, such as its priority. The credentials sent to the nodes in the transmission path may be similar to the credentials 400 illustrated in FIG. 4. For example, the credentials may include, but are not limited to, a patient identifier, a provider identifier, the identities of the requesting node, destination node, next node in the transmission path, and the previous node in the transmission path, a regulatory classification, a priority, a severity, a channel identifier, and a channel status. The credentials, or an application using the credentials, may act as a wrapper or abstraction layer on each node in order to format communication of the medical data to conform to the communications standard and to reserve the necessary resources of the node for transmission. The credentials may be stored in memory of the node.

The node may receive medical data through the transmission path according to the communications standard in block 1106.

In determination block 1108, the node may determine whether the topology of the network has changed. The node may be capable of communicating with a number of other nodes in the medical data network and may recognize when nodes are malfunctioning or have left the network, new nodes have been added, the location of nodes have changed, communication characteristics of other nodes have changed, or when other changes to the medical device network occur that may affect the transmission path.

In response to determining that the network topology has not changed (i.e. determination block 1108="No"), the node may determine whether the next node in the transmission path is able to receive the medical data in determination block 1110. For example, the node may attempt to establish communication with the next node to determine whether the attempt succeeds or fails.

In response to determining that the next node is able to receive the medical data (i.e. determination block 1110="Yes"), the node may transmit the medical data received from a previous node in the transmission path to the next node according to the communications standard in block 1112.

In response to determining that the network topology has changed (i.e. determination block 1108="Yes") or in response to determining that the next node is not able to receive the medical data (i.e. determination block 1110="No"), the node may determine a new transmission path in block 1114. In other words, in response to determining that the next node is not working properly or that the network topology has changed in some way that affects the transmission path (either positively or negatively), the node may generate a new transmission path, or alternatively may send a request to the server to generate a new transmission path.

In block 1116, the node may identify a new next node in the new transmission path. In embodiments in which the server generates the new transmission path, the node may receive the identity of the new next node from the server. The information may be included in updated credentials sent to the node from the server, in which the updated credentials are applicable to the new transmission path. The node may then transmit the medical data to the new next node according to the communications standard in block 1116. In some embodiments or situations, in response to a request for a new transmission path in block 1114, the node may implement new credentials or receive new credentials from the server in block 1104, and perform the operations of blocks 1106-1114 of the method 1100 as described above.

In determination block 1118, the node may determine whether the data transmissions passing through the node are complete. This determination may be made upon receiving a message from the server or another node indicating that the network should be torn down and/or the credentials should be deleted. Alternatively or in addition, the node may determine that data transmissions have ended when a predetermined duration has transpired since a last block of medical data was transmitted, such as through the expiration of a timer that is reset each time medical data is transmitted. So long as the data transmissions have not completed (i.e., determination block 1118="No"), the node may continue to receive medical data from the previous node in the network in block 1106 and perform the operations of blocks 1106-1120 of the method 1100 as described above.

In response to determining that the transmission of the medical data is complete (i.e., determination block 1118="No"), the node may delete or disable the credentials for that particular transmission path in block 1120. In this manner, the method 1100 provides a way for a node to participate in a medical data network, for example when the node is a general computing device that is not specifically configured to transmit regulated medical data, without requiring the node to be permanently configured as a medical network node.

Various embodiments may be implemented in any of a variety of communication devices, an example of which (e.g., multi-SIM communication device 1200) is illustrated in FIG. 1. The multi-SIM communication device 1200 may be similar to the smart phones 108, 250 and may implement the method 1100 described with reference to FIG. 11

The multi-SIM communication device 1200 may include a processor 1202 coupled to a touchscreen controller 1204 and an internal memory 1206. The processor 1202 may be one or more multi-core integrated circuits designated for general or specific processing tasks. The internal memory 1206 may be volatile or non-volatile memory, and may also be secure and/or encrypted memory, or unsecure and/or unencrypted memory, or any combination thereof. The touchscreen controller 1204 and the processor 1202 may also be coupled to a touchscreen panel 1212, such as a resistive-sensing touchscreen, capacitive-sensing touchscreen, infrared sensing touchscreen, etc. Additionally, the display of the multi-SIM communication device 1200 need not have touch screen capability.

The multi-SIM communication device 1200 may have one or more cellular network transceivers 1208 coupled to the processor 1202 and to one or more antennas 1210 and configured for sending and receiving cellular communications. The one or more transceivers 1208 and the one or more antennas 1210 may be used with the above-mentioned circuitry to implement various embodiment methods. The multi-SIM communication device 600 may include one or more SIM cards 1216 coupled to the one or more transceivers 608 and/or the processor 1202 and may be configured as described above.

The multi-SIM communication device 1200 may also include speakers 1214 for providing audio outputs. The multi-SIM communication device 1200 may also include a housing 1220, constructed of a plastic, metal, or a combination of materials, for containing all or some of the components discussed herein. The multi-SIM communication device 1200 may include a power source 1222 coupled to the processor 1202, such as a disposable or rechargeable battery. The rechargeable battery may also be coupled to the peripheral device connection port to receive a charging current from a source external to the multi-SIM communication device 1200. The multi-SIM communication device 600 may also include a physical button 1224 for receiving user inputs. The multi-SIM communication device 1200 may also include a power button 1226 for turning the multi-SIM communication device 1200 on and off.

Figure 13:
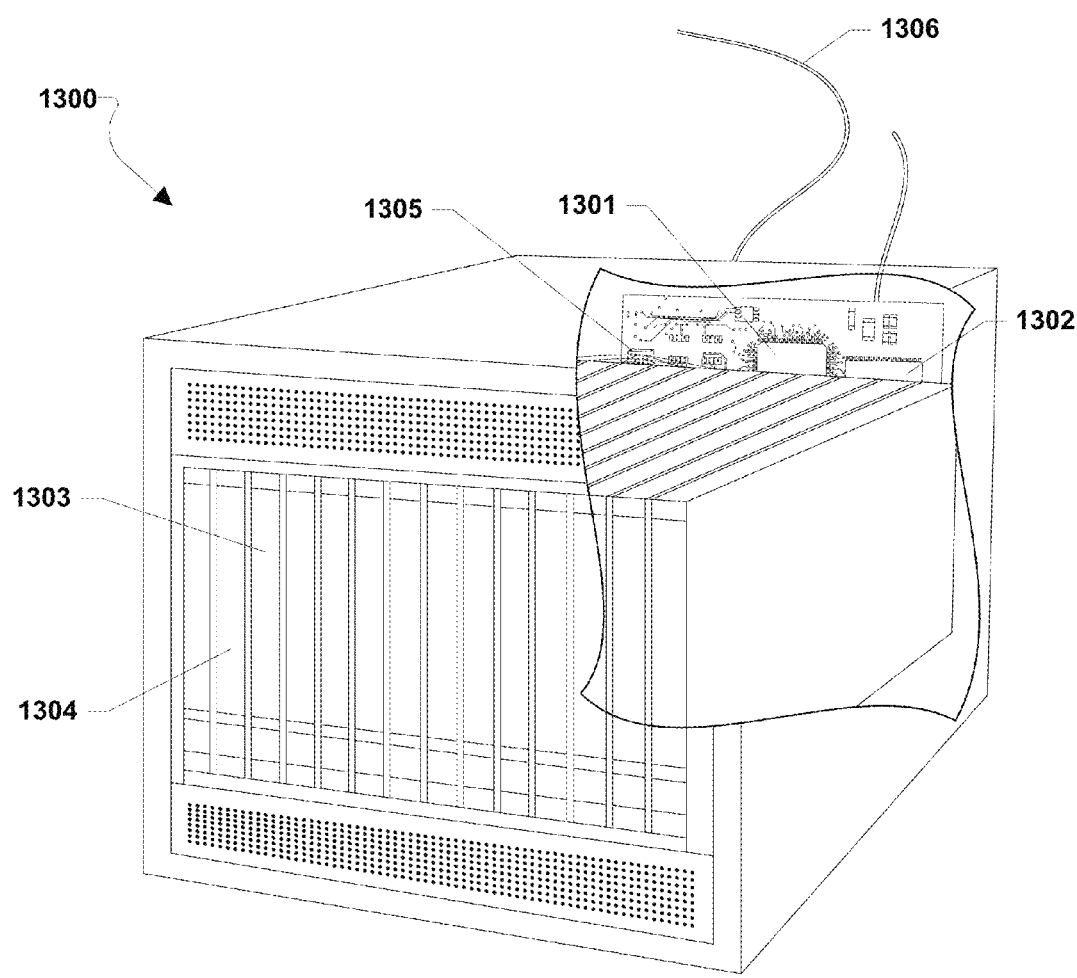
FIG. 13 is a component diagram of an example server suitable for use with the various embodiments.

Portions of some embodiment methods may be accomplished in a client-server architecture with some of the processing occurring in a server (e.g., the server 280, 502). Such embodiments may be implemented on any of a variety of commercially available server devices, such as server device 1300 illustrated in FIG. 13. As such, the server device 1300 may implement the methods 800, 900, and 1000 described with reference to FIGS. 8-10.

A server device 1300 may include a processor 1301 coupled to volatile memory 1302 and a large capacity nonvolatile memory, such as a disk drive 1303. The server device 1300 may also include a floppy disc drive, compact disc (CD) or digital versatile disc (DVD) disc drive 1304 coupled to the processor 1301. The server device 1300 may also include network access ports 1305 coupled to the processor 1301 for establishing data connections with a network 1306, such as a local area network coupled to nodes in a medical data network. The processor 1301 may be any programmable microprocessor, microcomputer or multiple processor chip or chips that can be configured by software instructions (applications) to perform a variety of functions, including the functions of the various aspects described above. Typically, software applications may be stored in the internal memories 1302, 1303 before they are accessed and loaded into the processor 1301. The processor 1301 may include internal memory sufficient to store the application software instructions.

The processors 206, 210, 222, 232, 234, 252, 262, 270, 271, 282, 286, 290, 1202 and 1301 may be any programmable microprocessor, microcomputer or multiple processor chip or chips that can be configured by software instructions (applications) to perform a variety of functions, including the functions of the various embodiments described above. In some devices, multiple processors may be provided, such as one processor dedicated to wireless communication functions and one processor dedicated to running other applications. Typically, software applications may be stored in the internal memory 208, 224, 254, 284, 1206, and 1302 before they are accessed and loaded into the processors 206, 210, 222, 232, 234, 252, 262, 270, 271, 282, 286, 290, 1202 and 1301. The processors 206, 210, 222, 232, 234, 252, 262, 270, 271, 282, 286, 290, 1202 and 1301 may include internal memory sufficient to store the application software instructions. In many devices the internal memory may be a volatile or nonvolatile memory, such as flash memory, or a mixture of both. For the purposes of this description, a general reference to memory refers to memory accessible by the processors 206, 210, 222, 232, 234, 252, 262, 270, 271, 282, 286, 290, 1202 and 1301 including internal memory or removable memory plugged into the computing device and memory within the 206, 210, 222, 232, 234, 252, 262, 270, 271, 282, 286, 290, 1202 and 1301 themselves.

The foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, DVD, floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present claims. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method for determining a network transmission path for medical data, comprising:
   receiving, on a server, a request from a requesting node to transmit medical data to a destination node;
   determining a list of nodes qualified ("qualified nodes") for use in establishing a network for transmitting the medical data to the destination node;
   determining at least one transmission path from the requesting node to the destination node using the list of qualified nodes;
   deputizing each node in the at least one transmission path by sending to each node in the at least one transmission path credentials that configure each node in the at least one transmission path to communicate the medical data according to a communications standard;
   instructing the requesting node to transmit the medical data through the at least one transmission path;
   determining whether a plurality of transmission paths share a common node;
   determining whether the common node is capable of supporting the plurality of transmission paths in response to determining that the plurality of transmission paths share the common node; and
   selecting one or more transmission paths in the plurality of transmission paths for the common node to support in response to determining that the common node is not capable of supporting the plurality of transmission paths.

2. The method of claim 1, further comprising verifying whether the requesting node is qualified to receive or transmit medical data and ignoring the request from the requesting node in response to determining that the requesting node is not qualified to receive or transmit medical data.

3. The method of claim 1, wherein determining the list of qualified nodes for use in establishing a network for transmitting the medical data to the destination node comprises:
   receiving communication characteristics of each node;
   determining whether each node is qualified to transmit the medical data based on communication characteristics of the node and the communications standard; and
   adding the node to the list of qualified nodes in response to determining that the node is qualified to transmit the medical data.

4. The method of claim 3, wherein the communication characteristics include at least one of a data reception rate, a data transmission rate, a communication interface type, a device type, a communications range, a device identifier, a medium access control address, an interface requirement, a bandwidth capability, a packet redundancy level, a quality of service level, a latency level, a security capability, a link redundancy level, and a power level.

5. The method of claim 1, wherein the credentials comprise at least one of a regulatory classification, a priority, a patient identifier, a provider identifier, a channel identifier, a channel status, the at least one transmission path, an identity of a previous node in the at least one transmission path, and an identity of a next node in the at least one transmission path.

6. The method of claim 1, further comprising de-deputizing each node in the at least one transmission path when transmission of the medical data is complete, wherein de-deputizing each node comprises disabling the credentials on each node.

7. The method of claim 1, further comprising:
   receiving a request from an intermediate node in the at least one transmission path to change the at least one transmission path;
   determining at least one alternate transmission path from the requesting node to the destination node using the list of qualified nodes;
   deputizing each node in the at least one alternate transmission path by sending each node in the at least one alternate transmission path credentials that configure each node in the at least one alternate transmission path to communicate the medical data according to the communications standard; and
   instructing the requesting node and the intermediate node to transmit the medical data through the at least one alternate transmission path.

8. The method of claim 1, wherein the communications standard is a medical regulatory standard.

9. The method of claim 1, wherein determining the at least one transmission path from the requesting node to the destination node using the list of qualified nodes comprises determining at least one of a total transmission distance, an available resources of each node in the at least one transmission path, a number of nodes in the at least one transmission path, and a characteristic of the medical data.

10. A method executed by a node of a network for transmitting medical data in the network, comprising:
    implementing credentials that configure the node to communicate medical data through a transmission path according to a communications standard;
    transmitting the medical data received from a previous node in the transmission path to a next node in the transmission path according to the communications standard,
    determining whether the node is shared by a plurality of transmission paths;
    determining whether the node is capable of supporting the plurality of transmission paths in response to determining that the node is shared by the plurality of transmission paths;

notifying a server that the node is not capable of supporting the plurality of transmission paths in response to determining that the node is not capable of supporting the plurality of transmission paths; and receiving an instruction from the server to support one or more transmission paths in the plurality of transmission paths in response to notifying the server that the node is not capable of supporting the plurality of transmission paths.

11. The method of claim 10, further comprising:
determining whether a topology of the network has changed or whether the next node is able to receive the medical data; and
determining an alternate transmission path in response to determining that the topology of the network has changed or that the next node is not able to receive the medical data.

12. The method of claim 10, wherein the node receives the credentials from the server in response to sending communication characteristics of the node to the server.

13. The method of claim 11, wherein the communication characteristics include at least one of a data reception rate, a data transmission rate, a communication interface type, a device type, a communications range, a device identifier, a medium access control address, an interface requirement, a bandwidth capability, a packet redundancy level, a quality of service level, a latency level, a security capability, a link redundancy level, and a power level.

14. The method of claim 10, wherein the credentials comprise at least one of a regulatory classification, a priority, a patient identifier, a provider identifier, a channel identifier, a channel status, the transmission path, an identity of the previous node in the transmission path, and an identity of the next node in the transmission path.

15. The method of claim 10, wherein the communications standard is a medical regulatory standard.

16. A server, comprising:
a processor configured with processor-executable instructions to:
receive a request from a requesting node to transmit medical data to a destination node;
determine a list of nodes qualified ("qualified nodes") for use in establishing a network for transmitting the medical data to the destination node;
determine at least one transmission path from the requesting node to the destination node using the list of qualified nodes;
deputize each node in the at least one transmission path by sending to each node in the at least one transmission path credentials that configure each node in the at least one transmission path to communicate the medical data according to a communications standard;
instruct the requesting node to transmit the medical data through the at least one transmission path;
determine whether a plurality of transmission paths share a common node;
determine whether the common node is capable of supporting the plurality of transmission paths in response to determining that the plurality of transmission paths share the common node; and
select one or more transmission paths in the plurality of transmission paths for the common node to support in response to determining that the common node is not capable of supporting the plurality of transmission paths.

17. The server of claim 16, wherein the processor is further configured with processor-executable instructions to verify whether the requesting node is qualified to receive or transmit medical data and ignore the request from the requesting node in response to determining that the requesting node is not qualified to receive or transmit medical data.

18. The server of claim 16, wherein the processor is further configured with processor-executable instructions to determine the list of qualified nodes for use in establishing a network for transmitting the medical data to the destination node by:
receiving communication characteristics of each node;
determining whether each node is qualified to transmit the medical data based on communication characteristics of the node and the communications standard; and
adding the node to the list of qualified nodes in response to determining that the node is qualified to transmit the medical data.

19. The server of claim 18, wherein the communication characteristics include at least one of a data reception rate, a data transmission rate, a communication interface type, a device type, a communications range, a device identifier, a medium access control address, an interface requirement, a bandwidth capability, a packet redundancy level, a quality of service level, a latency level, a security capability, a link redundancy level, and a power level.

20. The server of claim 16, wherein the credentials comprise at least one of a regulatory classification, a priority, a patient identifier, a provider identifier, a channel identifier, a channel status, the at least one transmission path, an identity of a previous node in the at least one transmission path, and an identity of a next node in the at least one transmission path.

21. The server of claim 16, wherein the processor is further configured with processor-executable instructions to de-deputize each node in the at least one transmission path when transmission of the medical data is complete, wherein de-deputizing each node comprises disabling the credentials on each node.

22. The server of claim 16, wherein the processor is further configured with processor-executable instructions to:
receive a request from an intermediate node in the at least one transmission path to change the at least one transmission path;
determine at least one alternate transmission path from the requesting node to the destination node using the list of qualified nodes;
deputize each node in the at least one alternate transmission path by sending each node in the at least one alternate transmission path credentials that configure each node in the at least one alternate transmission path to communicate the medical data according to the communications standard; and
instruct the requesting node and the intermediate node to transmit the medical data through the at least one alternate transmission path.

23. The server of claim 16, wherein the communications standard is a medical regulatory standard.

24. The server of claim 16, wherein the processor is further configured with processor-executable instructions to determine the at least one transmission path from the requesting node to the destination node using the list of qualified nodes by determining at least one of a total transmission distance, an available resources of each node in the at least one transmission path, a number of nodes in the at least one transmission path, and a characteristic of the medical data.

25. A node, comprising:
a processor configured with processor-executable instructions to:
- implement credentials that configure the node to communicate medical data through a transmission path according to a communications standard;
- transmit the medical data received from a previous node in the transmission path to a next node in the transmission path according to the communications standard;
- determine whether the node is shared by a plurality of transmission paths;
- determine whether the node is capable of supporting the plurality of transmission paths in response to determining that the node is shared by the plurality of transmission paths;
- notify a server that the node is not capable of supporting the plurality of transmission paths in response to determining that the node is not capable of supporting the plurality of transmission paths; and
- receive an instruction from the server to support one or more transmission paths in the plurality of transmission paths in response to notifying the server that the node is not capable of supporting the plurality of transmission paths.

26. The node of claim 25, wherein the processor is further configured with processor-executable instructions to:
- determine whether a topology of the network has changed or whether the next node is able to receive the medical data; and
- determine an alternate transmission path in response to determining that the topology of the network has changed or that the next node is not able to receive the medical data.

27. The node of claim 25, wherein the node receives the credentials from the server in response to sending communication characteristics of the node to the server.

28. The node of claim 25, wherein the communications standard is a medical regulatory standard.

* * * * *